US012697254B2

(12) United States Patent
Derrick

(10) Patent No.: US 12,697,254 B2
(45) Date of Patent: Aug. 4, 2026

(54) ANTIMICROBIAL/ANTIBACTERIAL DISRUPTIVE DRESSING FOR USE WITH NEGATIVE PRESSURE AND FLUID INSTILLATION

(71) Applicant: Solventum Intellectual Properties Company, Maplewood, MN (US)

(72) Inventor: Kathleen L. Derrick, San Antonio, TX (US)

(73) Assignee: Solventum Intellectual Properties Company, Maplewood, MN (US)

( * ) Notice: Subject to any disclaimer, the term of this patent is extended or adjusted under 35 U.S.C. 154(b) by 269 days.

(21) Appl. No.: 17/629,174

(22) PCT Filed: Jul. 22, 2020

(86) PCT No.: PCT/IB2020/056911
§ 371 (c)(1),
(2) Date: Jan. 21, 2022

(87) PCT Pub. No.: WO2021/019371
PCT Pub. Date: Feb. 4, 2021

(65) Prior Publication Data
US 2022/0249291 A1 Aug. 11, 2022

Related U.S. Application Data

(60) Provisional application No. 62/878,812, filed on Jul. 26, 2019.

(51) Int. Cl.
*A61F 13/00* (2024.01)
*A61F 13/05* (2024.01)
(Continued)

(52) U.S. Cl.
CPC ........ *A61F 13/00063* (2013.01); *A61F 13/05* (2024.01); *A61L 15/44* (2013.01);
(Continued)

(58) Field of Classification Search
CPC .... A61F 13/00; A61F 13/00063; A61F 13/02; A61F 13/05; A61F 13/01017;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Copper Development Association Inc., Introduction to Antimicrobial Copper, Feb. 15, 2014.*
(Continued)

*Primary Examiner* — Alireza Nia
*Assistant Examiner* — Andrew Jun-Wai Mok

(57) ABSTRACT

Dressings, systems, and methods for treating a tissue site are described herein. The dressing has a contact layer having a plurality of holes. The contact layer is configured to be positioned adjacent to the tissue site. The dressing also includes a cover layer having a first side configured to be positioned adjacent to the contact layer and a second side opposite the first side. An antimicrobial agent is coupled to the first side of the cover layer. The dressing has a drape configured to be positioned over the cover layer to form a sealed space having the contact layer and the cover layer disposed in the sealed space.

6 Claims, 11 Drawing Sheets

(51) Int. Cl.
    *A61L 15/44*        (2006.01)
    *A61L 15/46*        (2006.01)

(52) U.S. Cl.
    CPC ......... *A61L 15/46* (2013.01); *A61L 2300/104*
        (2013.01); *A61L 2300/404* (2013.01); *A61L*
        *2300/45* (2013.01)

(58) Field of Classification Search
    CPC ............ A61F 13/01034; A61F 13/0203; A61F
        13/0206; A61F 13/0209; A61F 13/022;
        A61F 13/0223; A61F 13/0226; A61F
        13/0243; A61F 13/0246; A61F 13/0253;
        A61F 13/0256; A61F 13/0266; A61L
        15/44; A61L 15/46; A61L 15/225; A61L
        15/425; A61L 2300/104; A61L 2300/404;
        A61L 2300/45
    See application file for complete search history.

(56)           References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,683,921 | A | 8/1972 | Brooks et al. |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,902,565 | A | 2/1990 | Brook |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,765,123 | B2 | 7/2004 | de Jong et al. |
| 6,814,079 | B2 | 11/2004 | Heaton et al. |
| 7,381,859 | B2 | 6/2008 | Hunt et al. |
| 7,846,141 | B2 | 12/2010 | Weston |
| 7,951,124 | B2 | 5/2011 | Boehringer et al. |
| 8,062,273 | B2 | 11/2011 | Weston |
| 8,216,198 | B2 | 7/2012 | Heagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,168,180 | B2 | 10/2015 | Ha et al. |
| 9,198,801 | B2 | 12/2015 | Weston |
| 9,211,365 | B2 | 12/2015 | Weston |
| 9,289,542 | B2 | 3/2016 | Blott et al. |
| 9,421,309 | B2 | 8/2016 | Robinson et al. |
| 9,918,733 | B2 | 3/2018 | Ingram et al. |
| 9,974,694 | B2 | 5/2018 | Locke et al. |
| 10,369,058 | B2 | 8/2019 | Ha et al. |
| 10,610,414 | B2 | 4/2020 | Hartwell et al. |
| 10,736,788 | B2 | 8/2020 | Locke et al. |
| 10,743,900 | B2 | 8/2020 | Ingram et al. |
| 11,224,542 | B2 | 1/2022 | Robinson et al. |
| 2001/0037118 | A1 | 11/2001 | Shadduck |
| 2002/0065494 | A1 | 5/2002 | Lockwood et al. |
| 2002/0077661 | A1 | 6/2002 | Saadat |

(56) References Cited

U.S. PATENT DOCUMENTS

| | | |
|---|---|---|
| 2002/0115951 A1 | 8/2002 | Norstrem et al. |
| 2002/0120185 A1 | 8/2002 | Johnson |
| 2002/0143286 A1 | 10/2002 | Tumey |
| 2002/0161346 A1 | 10/2002 | Lockwood et al. |
| 2004/0030304 A1* | 2/2004 | Hunt ..................... A61L 15/425 |
| | | 604/317 |
| 2005/0282895 A1* | 12/2005 | Dosch ................. A61K 31/194 |
| | | 514/557 |
| 2007/0185426 A1 | 8/2007 | Ambrosio et al. |
| 2008/0132819 A1 | 6/2008 | Radl et al. |
| 2008/0177253 A1 | 7/2008 | Boehringer et al. |
| 2008/0275409 A1 | 11/2008 | Kane et al. |
| 2008/0300555 A1 | 12/2008 | Olson et al. |
| 2009/0012482 A1 | 1/2009 | Pinto et al. |
| 2009/0069760 A1 | 3/2009 | Finklestein |
| 2009/0093779 A1 | 4/2009 | Riesinger |
| 2009/0227969 A1 | 9/2009 | Jaeb et al. |
| 2009/0299303 A1 | 12/2009 | Seegert |
| 2010/0063484 A1 | 3/2010 | Heagle |
| 2010/0160871 A1 | 6/2010 | Seegert et al. |
| 2010/0160874 A1 | 6/2010 | Robinson et al. |
| 2010/0160876 A1 | 6/2010 | Robinson et al. |
| 2010/0185163 A1 | 7/2010 | Heagle |
| 2010/0312159 A1 | 12/2010 | Aali et al. |
| 2011/0015619 A1 | 1/2011 | Svedman et al. |
| 2011/0054422 A1 | 3/2011 | Locke et al. |
| 2011/0087176 A2 | 4/2011 | Blott et al. |
| 2011/0118683 A1 | 5/2011 | Weston |
| 2011/0178451 A1 | 7/2011 | Robinson et al. |
| 2011/0213287 A1 | 9/2011 | Lattimore et al. |
| 2011/0213319 A1 | 9/2011 | Blott et al. |
| 2011/0230809 A1 | 9/2011 | Manwaring et al. |
| 2011/0282309 A1 | 11/2011 | Adie et al. |
| 2011/0301556 A1 | 12/2011 | Lichtenstein |
| 2012/0016334 A1 | 1/2012 | Nakajima et al. |
| 2012/0143113 A1 | 6/2012 | Robinson et al. |
| 2012/0143114 A1 | 6/2012 | Locke et al. |
| 2012/0157945 A1 | 6/2012 | Robinson et al. |
| 2013/0144230 A1 | 6/2013 | Wu et al. |
| 2013/0211349 A1 | 8/2013 | Stokes et al. |
| 2013/0274717 A1 | 10/2013 | Dunn |
| 2014/0066868 A1 | 3/2014 | Freedman et al. |
| 2014/0155791 A1 | 6/2014 | Robinson et al. |
| 2014/0163491 A1 | 6/2014 | Schuessler et al. |
| 2014/0228787 A1 | 8/2014 | Croizat et al. |
| 2014/0236112 A1* | 8/2014 | Von Wolff ........ A61F 13/15577 |
| | | 156/244.11 |
| 2015/0080788 A1 | 3/2015 | Blott et al. |
| 2015/0119832 A1* | 4/2015 | Locke ............... A61F 13/00063 |
| | | 604/319 |
| 2015/0174284 A1 | 6/2015 | Payne et al. |
| 2015/0201954 A1 | 7/2015 | Pratt et al. |
| 2015/0320434 A1* | 11/2015 | Ingram ................... A61M 1/85 |
| | | 606/131 |
| 2015/0320602 A1 | 11/2015 | Locke et al. |
| 2015/0320603 A1 | 11/2015 | Locke et al. |
| 2016/0022885 A1 | 1/2016 | Dunn et al. |
| 2016/0038345 A1 | 2/2016 | Ha et al. |
| 2016/0095754 A1 | 4/2016 | Andrews et al. |
| 2016/0158066 A1 | 6/2016 | Chao |
| 2016/0175156 A1 | 6/2016 | Locke et al. |
| 2016/0354086 A1 | 12/2016 | Dunn |
| 2017/0007462 A1 | 1/2017 | Hartwell et al. |
| 2017/0135862 A1 | 5/2017 | Tuck et al. |
| 2017/0189237 A1 | 7/2017 | Locke et al. |
| 2017/0197006 A1* | 7/2017 | Johnson ............ A61F 13/00063 |
| 2017/0231822 A1* | 8/2017 | Hoggarth ................ A61L 15/26 |
| | | 604/360 |
| 2017/0239095 A1 | 8/2017 | Hoggarth et al. |
| 2018/0235646 A1 | 8/2018 | Locke et al. |
| 2018/0353337 A1 | 12/2018 | Locke |
| 2018/0353338 A1 | 12/2018 | Locke et al. |
| 2018/0353662 A1 | 12/2018 | Locke et al. |
| 2019/0117465 A1* | 4/2019 | Osborne ................. A61F 13/05 |
| 2019/0192350 A1 | 6/2019 | Gowans et al. |
| 2019/0231944 A1 | 8/2019 | Dunn et al. |
| 2019/0274889 A1 | 9/2019 | Steward et al. |
| 2019/0314209 A1 | 10/2019 | Ha et al. |
| 2020/0046567 A1 | 2/2020 | Carroll et al. |
| 2020/0107965 A1 | 4/2020 | Greener |
| 2020/0146896 A1 | 5/2020 | Rice et al. |
| 2020/0155359 A1 | 5/2020 | Carroll et al. |
| 2020/0383837 A1 | 12/2020 | Gowans et al. |
| 2021/0077302 A1 | 3/2021 | Carroll et al. |
| 2021/0228417 A1 | 7/2021 | Ha et al. |
| 2023/0000687 A1 | 1/2023 | Rice et al. |
| 2023/0000688 A1 | 1/2023 | Rice et al. |
| 2024/0099898 A1 | 3/2024 | Rice et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| DE | 102006017194 A1 | 10/2007 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 2098257 A1 | 9/2009 |
| EP | 3263079 A1 | 1/2018 |
| EP | 3378450 A1 | 9/2018 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| GB | 2365350 A | 2/2002 |
| GB | 2377939 A | 1/2003 |
| JP | S57-013040 A | 1/1982 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 0185248 A1 | 11/2001 |
| WO | 2005102234 A2 | 11/2005 |
| WO | 2006114638 A2 | 11/2006 |
| WO | 2008/005532 A2 | 1/2008 |
| WO | 2008136998 A1 | 11/2008 |
| WO | 2009021523 A1 | 2/2009 |
| WO | 2009/146441 A1 | 12/2009 |
| WO | 2010051071 A1 | 5/2010 |
| WO | 2010051073 A1 | 5/2010 |
| WO | 2010075178 A2 | 7/2010 |
| WO | 2011008497 A2 | 1/2011 |
| WO | 2011089098 A1 | 7/2011 |
| WO | 2013/032745 A1 | 3/2013 |
| WO | 2013066426 A2 | 5/2013 |
| WO | 2013071243 A2 | 5/2013 |
| WO | 2013116552 A1 | 8/2013 |
| WO | 2013129343 A1 | 9/2013 |
| WO | 2013149078 A1 | 10/2013 |
| WO | 2014/014922 A1 | 1/2014 |
| WO | 2014014871 A1 | 1/2014 |
| WO | 2014024048 A1 | 2/2014 |
| WO | 2014143487 A1 | 9/2014 |
| WO | 2015172104 A1 | 11/2015 |
| WO | 2015173547 A1 | 11/2015 |
| WO | WO-2015172111 A1 * | 11/2015 ............. A61B 17/32 |
| WO | 2017195038 A1 | 11/2017 |
| WO | 2018/077872 A1 | 5/2018 |
| WO | 2018/094061 A1 | 5/2018 |

(56)     References Cited

FOREIGN PATENT DOCUMENTS

| WO | 2018/226328 A1 | 12/2018 |
| WO | 2019136164 A1 | 7/2019 |
| WO | 2019152422 A1 | 8/2019 |
| WO | 2020097529 A1 | 5/2020 |

OTHER PUBLICATIONS

Office Action for related U.S. Appl. No. 16/678,450, dated Jul. 31, 2023.
Office Action for related U.S. Appl. No. 16/923,651, dated Aug. 28, 2023.
Office action for related U.S. Appl. No. 16/918,682, dated Sep. 21, 2023.
Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
Partial International Search Report from PCT/US2015/030030 mailed Jul. 22, 2015.

(56)                References Cited

OTHER PUBLICATIONS

International Search Report and Written Opinion for PCT/US2015/030023 mailed Aug. 24, 2015.

Extended European Search Report for corresponding Application No. 171862527, mailed Nov. 14, 2017.

"Introduction to Polyurethanes: Thermoplastic Polyurethane", American Chemistry Council, 2018, https://polyurethane.americanchemistry.com/polyurethanes/Introduction-to-Polyurethanes/Applications/Thermoplastic-Polyurethane/.

International Search Report and Written Opinion for PCT/US2015/030027 mailed Jul. 15, 2015.

International Search Report and Written Opinion for corresponding Application No. PCT/US2019/027463, mailed Jul. 4, 2019.

Japanese Notice of Rejection for corresponding Application No. 2016-566815, mailed Feb. 5, 2019.

Extended European Search Report for corresponding Application No. 18162504.7, mailed May 24, 2018.

Japanese Notice of Rejection for corresponding Application No. 2016-566785, mailed Jun. 25, 2019.

Japanese Notice of Rejection for corresponding Application No. 2016-566785, mailed Jan. 29, 2019.

Non-Final Office Action for Corresponding U.S. Appl. No. 15/960,310, mailed Apr. 29, 2020.

Japanese Notice of Rejection for Corresponding Application No. 2019-233695, mailed Oct. 13, 2020.

International Search Report and Written Opinion for Corresponding Application No. PCT/US2019/060567, mailed Feb. 14, 2020.

International Search Report and Written Opinion for Corresponding Application No. PCT/US2019/045505, mailed Nov. 7, 2019.

International Search Report and Written Opinion for Corresponding Application No. PCT/US2019/060479, mailed Apr. 7, 2020.

International Search Report and Written Opinion for Corresponding Application No. PCT/US2020/013922, mailed May 4, 2020.

Chinese Notice of Rejection Corresponding to Application No. 2020800099951, mailed Mar. 28, 2022.

International Search Report and Written Opinion Corresponding to Application No. PCT/IB2020/061435, mailed Mar. 16, 2021.

International Search Report and Written Opinion Corresponding to Application No. PCT/IB2020/061465, mailed Mar. 16, 2021.

International Search Report and Written Opinion Corresponding to Application No. PCT/IB2020/061540, mailed Feb. 24, 2021.

Canadian Examination Report for related application 2,947,302, dated Jun. 11, 2021.

Japanese Notice of Rejection for related application 2020-557257, dated Feb. 28, 2023.

Office action for U.S. Appl. No. 16/678,450, dated Sep. 9, 2024.

Japanese Notice of Rejection for Application No. 2021-542412, dated Dec. 5, 2023.

European Examination Report for Application No. 20747133.5, dated Dec. 21, 2023.

Office action for related U.S. Appl. No. 16/923,651 dated Feb. 12, 2024.

Japanese Notice of Rejection for Application No. 2019-233695 dated Mar. 5, 2024.

International Search Report and Written Opinion for Corresponding Application No. PCT/IB2020/056911, mailed Oct. 21, 2020.

Japanese Notice of Rejection for Application No. 2021-524440 dated Apr. 16, 2024.

Office action for U.S. Appl. No. 16/745,075, dated Jul. 24, 2024.

Japanese Decision of Rejection and Decision for Dismissal of Amendment for Application No. 2021-524440, dated Oct. 15, 2024.

Office action for U.S. Appl. No. 16/918,682, dated Jan. 2, 2025.

Office action for U.S. Appl. No. 17/779,755, dated Apr. 9, 2025.

Office action for U.S. Appl. No. 17/779,792, dated Jun. 3, 2025.

Office Action for related U.S. Appl. No. 18/538,282, dated Nov. 10, 2025.

Office Action for related U.S. Appl. No. 17/779,755, dated Jan. 8, 2026.

Office Action for related U.S. Appl. No. 16/745,075, dated Jan. 28, 2026.

* cited by examiner

ANTIMICROBIAL/ANTIBACTERIAL DISRUPTIVE DRESSING FOR USE WITH NEGATIVE PRESSURE AND FLUID INSTILLATION

CROSS-REFERENCE TO RELATED APPLICATIONS

This application claims the benefit of priority to U.S. Provisional Application No. 62/878,812, filed on Jul. 26, 2019, which is incorporated herein by reference in its entirety.

TECHNICAL FIELD

The invention set forth in the appended claims relates generally to tissue treatment systems and more particularly, but without limitation, to a dressing for the removal of thick exudate having antibacterial and antimicrobial properties.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and instillation therapy are widely known, improvements to therapy systems, components, and processes may benefit healthcare providers and patients.

BRIEF SUMMARY

New and useful systems, apparatuses, and methods for decreasing bio-burden in a negative-pressure therapy environment are set forth in the appended claims. Illustrative embodiments are also provided to enable a person skilled in the art to make and use the claimed subject matter.

For example, in some embodiments, a dressing for treating a tissue site is described. The dressing can include a contact layer having a plurality of holes. The contact layer can be configured to be positioned adjacent to the tissue site. The dressing can also include a cover layer having a first side configured to be positioned adjacent to the contact layer and a second side opposite the first side. An antimicrobial agent can be coupled to the first side of the cover layer. The dressing can also include a drape configured to be positioned over the cover layer to form a sealed space having the contact layer and the cover layer disposed in the sealed space.

More generally, a dressing for treating a tissue site is described. The dressing may include a debridement tool having a plurality of openings extending through the debridement tool to form surfaces perpendicular to and extending from a first side to a second side of the debridement tool. The debridement tool can be configured to be positioned adjacent to the tissue site. An antibacterial agent can be coupled to the surfaces of the debridement tool. The dressing can include a drape configured to be positioned over the debridement tool to form a sealed space having the debridement tool disposed in the sealed space.

Alternatively, other example embodiments may provide an apparatus for debriding a tissue site with negative pressure. The apparatus can include a felted foam having a plurality of perforations, the perforations fluidly coupling a first side of the felted foam to a second side of the felted foam. A film can be coupled to the first side of the felted foam. The film may have an anti-bioburden agent.

A system for treating a tissue site with negative pressure is also described herein, wherein some example embodiments include a contact layer having a plurality of holes, the contact layer configured to be positioned adjacent to the tissue site. A cover layer having a first side configured to be positioned adjacent to the contact layer and a second side opposite the first side can be included in the system. An anti-bioburden agent can be coupled to the first side of the cover layer. The system can also include a drape configured to be positioned over the cover layer to form a sealed space having the contact layer and the cover layer disposed in the sealed space. A negative-pressure source can be configured to be fluidly coupled to the sealed space.

A method for treating a tissue site with negative pressure may also be described. A contact layer having a plurality of holes can be provided and positioned adjacent to the tissue site. In some embodiments, a cover layer having a first side and a second side opposite the first side can be provided. The first side of the cover layer can have an anti-bioburden agent. The first side of the cover layer can be positioned adjacent to the contact layer. A drape may be positioned over the cover layer to form a sealed space having the contact layer and the cover layer disposed in the sealed space. A negative-pressure source can be coupled to the sealed space and can supply negative-pressure to the sealed space.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

The term "tissue site" in this context broadly refers to a wound, defect, or other treatment target located on or within tissue, including but not limited to, a surface wound, bone tissue, adipose tissue, muscle tissue, neural tissue, dermal tissue, vascular tissue, connective tissue, cartilage, tendons, or ligaments. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted. A surface wound, as used herein, is a wound on the surface of a body that is exposed to the outer surface of the body, such an injury or damage to the epidermis, dermis, and/or subcutaneous layers. Surface wounds may include ulcers or closed incisions, for example. A surface wound, as used herein, does not include wounds within an intra-abdominal cavity. A wound may include chronic, acute, traumatic, subacute, and dehisced wounds, partial-thickness burns, ulcers (such as diabetic, pressure, or venous insufficiency ulcers), flaps, and grafts, for example.

Figure 1:
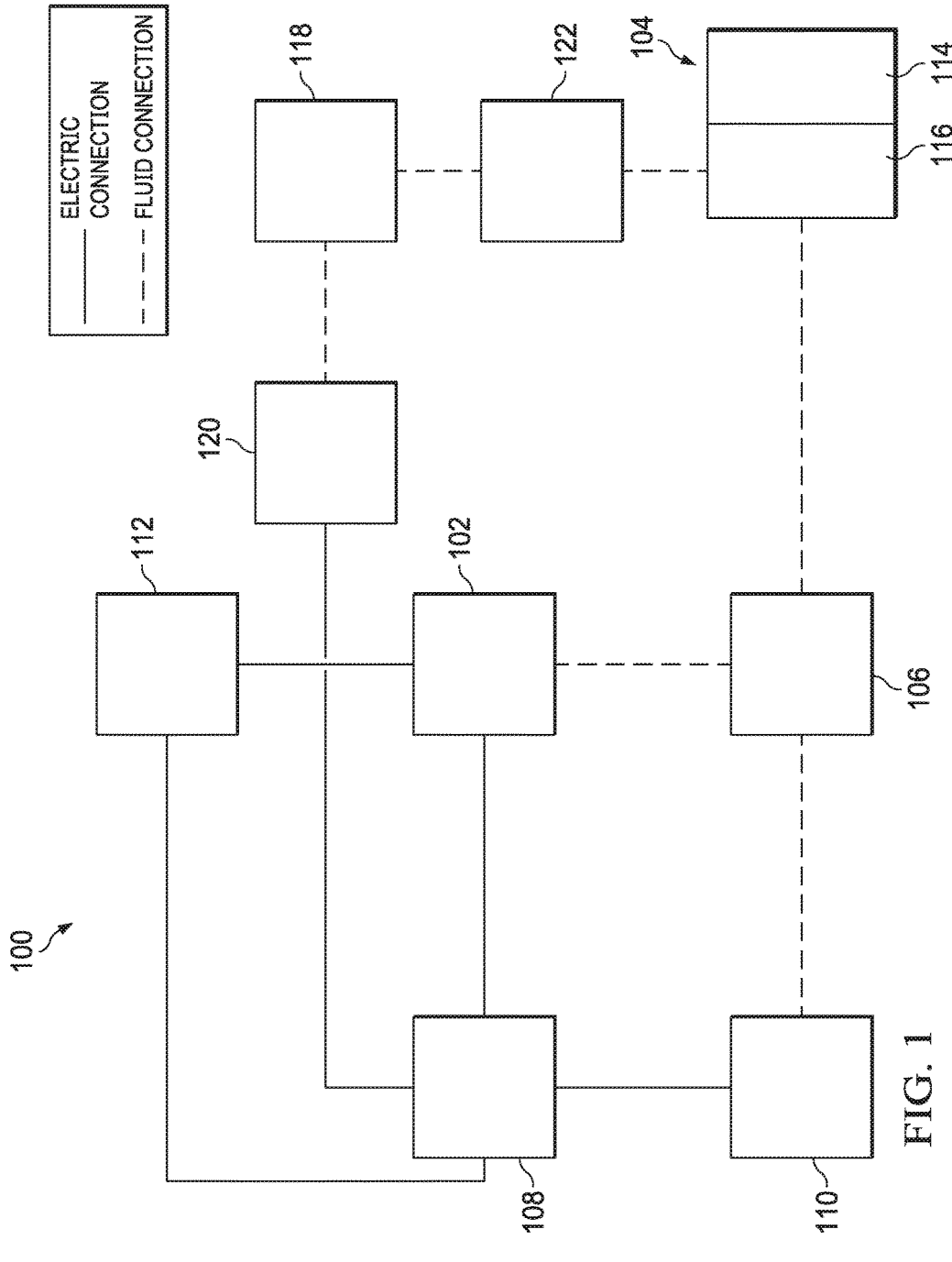
FIG. 1 is a simplified functional block diagram of an example embodiment of a therapy system that can provide negative-pressure therapy with instillation of topical treatment solutions to a tissue site in accordance with this specification.

FIG. 1 is a simplified functional block diagram of an example embodiment of a therapy system 100 that can provide negative-pressure therapy with instillation of topical treatment solutions to a tissue site in accordance with this specification. The therapy system 100 may include a source or supply of negative pressure, such as a negative-pressure source 102, a dressing 104, a fluid container, such as a container 106, and a regulator or controller, such as a controller 108, for example. Additionally, the therapy system 100 may include sensors to measure operating parameters and provide feedback signals to the controller 108 indicative of the operating parameters. As illustrated in FIG. 1, for example, the therapy system 100 may include a pressure sensor 110, an electric sensor 112, or both, coupled to the controller 108. As illustrated in the example of FIG. 1, the dressing 104 may comprise or consist essentially of a tissue interface 114, a cover 116, or both in some embodiments.

The therapy system 100 may also include a source of installation solution. For example, a solution source 118 may be fluidly coupled to the dressing 104, as illustrated in the example embodiment of FIG. 1. The solution source 118 may be fluidly coupled to a positive-pressure source such as the positive-pressure source 120, a negative-pressure source such as the negative-pressure source 102, or both in some embodiments. A regulator, such as an instillation regulator 122, may also be fluidly coupled to the solution source 118 and the dressing 104 to ensure proper dosage of instillation solution (e.g. saline or sterile water) to a tissue site. For example, the instillation regulator 122 may comprise a piston that can be pneumatically actuated by the negative-pressure source 102 to draw instillation solution from the solution source during a negative-pressure interval and to instill the solution to a dressing during a venting interval. Additionally or alternatively, the controller 108 may be coupled to the negative-pressure source 102, the positive-pressure source 120, or both, to control dosage of instillation solution to a tissue site. In some embodiments, the installation regulator 122 may also be fluidly coupled to the negative-pressure source 102 through the dressing 104, as illustrated in the example of FIG. 1.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 102 may be combined with the solution source 118, the controller 108, and other components into a therapy unit.

In general, components of the therapy system 100 may be coupled directly or indirectly. For example, the negative-pressure source 102 may be directly coupled to the container 106, and may be indirectly coupled to the dressing 104 through the container 106. Coupling may include fluid, mechanical, thermal, electrical, or chemical coupling (such as a chemical bond), or some combination of coupling in some contexts. For example, the negative-pressure source 102 may be electrically coupled to the controller 108, and may be fluidly coupled to one or more distribution components to provide a fluid path to a tissue site. In some embodiments, components may also be coupled by virtue of physical proximity, being integral to a single structure, or being formed from the same piece of material. For example, the tissue interface 114 and the cover 116 may be discrete layers disposed adjacent to each other, and may be joined together in some embodiments.

A distribution component is preferably detachable, and may be disposable, reusable, or recyclable. The dressing 104 and the container 106 are illustrative of distribution components. A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 104.

A negative-pressure supply, such as the negative-pressure source 102, may be a reservoir of air at a negative pressure, or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 106 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 108, may be a microprocessor or computer programmed to operate one or more components of the therapy system 100, such as the negative-pressure source 102. In some embodiments, for example, the controller 108 may be a microcontroller, which generally comprises an integrated circuit containing a processor core and a memory programmed to directly or indirectly control one or more operating parameters of the therapy system 100. Operating parameters may include the power applied to the negative-pressure source 102, the pressure generated by the negative-pressure source 102, or the pressure distributed to the tissue interface 114, for example. The controller 108 is also preferably configured to receive one or more input signals, such as a feedback signal, and programmed to modify one or more operating parameters based on the input signals.

Sensors, such as the pressure sensor 110 or the electric sensor 112, are generally known in the art as any apparatus operable to detect or measure a physical phenomenon or property, and generally provide a signal indicative of the phenomenon or property that is detected or measured. For example, the pressure sensor 110 and the electric sensor 112 may be configured to measure one or more operating parameters of the therapy system 100. In some embodiments, the pressure sensor 110 may be a transducer configured to measure pressure in a pneumatic pathway and convert the measurement to a signal indicative of the pressure measured. In some embodiments, the pressure sensor 110 may be a piezoresistive strain gauge. The electric sensor 112 may optionally measure operating parameters of the negative-pressure source 102, such as the voltage or current, in some embodiments. Preferably, the signals from the pressure sensor 110 and the electric sensor 112 are suitable as an input signal to the controller 108, but some signal conditioning may be appropriate. For example, the signal may need to be filtered or amplified before it can be processed by the controller 108. Typically, the signal is an electrical signal, but may be represented in other forms, such as an optical signal.

The tissue interface 114 can be generally adapted to partially or fully contact a tissue site. The tissue interface 114 may take many forms, and may have many sizes, shapes, or thicknesses depending on a variety of factors, such as the type of treatment being implemented or the nature and size of a tissue site. For example, the size and shape of the tissue interface 114 may be adapted to the contours of deep and irregular shaped tissue sites.

In some embodiments, the cover 116 may provide a bacterial barrier and protection from physical trauma. The cover 116 may also be constructed from a material that can reduce evaporative losses and provide a fluid seal between two components or two environments, such as between a therapeutic environment and a local external environment. The cover 116 may be, for example, an elastomeric film or membrane that can provide a seal adequate to maintain a negative pressure at a tissue site for a given negative-pressure source. The cover 116 may have a high moisture-vapor transmission rate (MVTR) in some applications. For example, the MVTR may be at least about 300 g/m$^2$ per twenty-four hours in some embodiments. In some example embodiments, the cover 116 may be a polymer drape, such as a polyurethane film, that is permeable to water vapor but impermeable to liquid. Such drapes typically have a thickness in the range of about 25 microns to about 50 microns. For permeable materials, the permeability generally should be low enough that a desired negative pressure may be maintained.

The cover 116 may comprise, for example, one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Coveris Advanced Coatings of Wrexham, United Kingdom having, for example, an MVTR (inverted cup technique) of about 14400 g/m$^2$/24 hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Glendale, California; polyether block polyamide copolymer (PEBAX), for example, from Arkema, France; INSPIRE 2327; or other appropriate material.

An attachment device may be used to attach the cover 116 to an attachment surface, such as undamaged epidermis, a gasket, or another cover. The attachment device may take many forms. For example, an attachment device may be a medically-acceptable, pressure-sensitive adhesive configured to bond the cover 116 to epidermis around a tissue site. In some embodiments, for example, some or all of the cover 116 may be coated with an adhesive, such as an acrylic adhesive, which may have a coating weight between about 25 grams per square meter (g.s.m.) to about 65 g.s.m. Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The solution source 118 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies a position in a fluid path relatively closer to a source of negative pressure or further away from a source of positive pressure. Conversely, the term "upstream" implies a position relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

During treatment of a tissue site, a biofilm may develop on or in the tissue site. Biofilms can comprise a microbial infection that can cover a tissue site and impair healing of the tissue site. Biofilms can also lower the effectiveness of topical antibacterial treatments by preventing the topical treatments from reaching the tissue site. The presence of biofilms can increase healing times, reduce the efficacy and efficiency of various treatments, and increase the risk of a more serious infection. Often, the application of an antibacterial or antimicrobial treatment may require removal of the overlying dressing. Repeated removal of the overlying dressing may cause pain or other trauma to a patient that may prolong a normal treatment period.

Even in the absence of biofilms, some tissue sites may not heal according to the normal medical protocol and may develop areas of necrotic tissue. Necrotic tissue may be dead tissue resulting from infection, toxins, or trauma that caused the tissue to die faster than the tissue can be removed by the normal body processes that regulate the removal of dead tissue. Sometimes, necrotic tissue may be in the form of slough, which may include a viscous liquid mass of tissue. Generally, slough is produced by bacterial and fungal infections that stimulate an inflammatory response in the tissue. Slough may be a creamy yellow color and may also be referred to as pus. Necrotic tissue may also include eschar. Eschar may be a portion of necrotic tissue that has become dehydrated and hardened. Eschar may be the result of a burn injury, gangrene, ulcers, fungal infections, spider bites, or anthrax. Eschar may be difficult to move without the use of surgical cutting instruments.

The tissue site may include biofilms, necrotic tissue, lacerated tissue, devitalized tissue, contaminated tissue, damaged tissue, infected tissue, exudate, highly viscous exudate, fibrinous slough and/or other material that can generally be referred to as debris. The debris may inhibit the efficacy of tissue treatment and slow the healing of the tissue site. If the debris is in the tissue site, the tissue site may be treated with different processes to disrupt the debris. Examples of disruption can include softening of the debris, separation of the debris from desired tissue, such as the subcutaneous tissue, preparation of the debris for removal from the tissue site, and removal of the debris from the tissue site.

The debris can require debridement performed in an operating room. In some cases, tissue sites requiring debridement may not be life-threatening, and debridement may be considered low-priority. Low-priority cases can experience delays prior to treatment as other, more life-threatening, cases may be given priority for an operating room. As a result, low priority cases may need temporization. Temporization can include stasis of a tissue site that limits deterioration of the tissue site prior to other treatments, such as debridement, negative-pressure therapy or instillation.

When debriding, clinicians may find it difficult to define separation between healthy, vital tissue and necrotic tissue. As a result, normal debridement techniques may remove too much healthy tissue or not enough necrotic tissue. If non-viable tissue demarcation does not extend deeper than the deep dermal layer, or if the tissue site is covered by the debris, such as slough or fibrin, gentle methods to remove the debris should be considered to avoid excess damage to the tissue site.

Debridement may include the removal of the debris. In some debridement processes, a mechanical process is used to remove the debris. Mechanical processes may include using scalpels or other cutting tools having a sharp edge to cut away the debris from the tissue site. Other mechanical processes may use devices that can provide a stream of particles to impact the debris to remove the debris in an abrasion process, or jets of high pressure fluid to impact the debris to remove the debris using water-jet cutting or lavage. Typically, mechanical processes of debriding a tissue site may be painful and may require the application of local anesthetics. Mechanical processes also risk over removal of healthy tissue that can cause further damage to the tissue site and delay the healing process.

Debridement may also be performed with an autolytic process. For example, an autolytic process may involve using enzymes and moisture produced by a tissue site to soften and liquefy the necrotic tissue and debris. Typically, a dressing may be placed over a tissue site having debris so that fluid produced by the tissue site may remain in place, hydrating the debris. Autolytic processes can be pain-free, but autolytic processes are a slow and can take many days. Because autolytic processes are slow, autolytic processes may also involve many dressing changes. Some autolytic processes may be paired with negative-pressure therapy so that, as debris hydrates, negative pressure supplied to a tissue site may draw off the debris. In some cases, a manifold positioned at a tissue site to distribute negative-pressure across the tissue site may become blocked or clogged with debris broken down by an autolytic process. If a manifold becomes clogged, negative-pressure may not be able to remove debris, which can slow or stop the autolytic process.

Debridement may also be performed by adding enzymes or other agents to the tissue site that digest tissue. Often, strict control of the placement of the enzymes and the length of time the enzymes are in contact with a tissue site must be maintained. If enzymes are left on a tissue site for longer than needed, the enzymes may remove too much healthy tissue, contaminate the tissue site, or be carried to other areas of a patient. Once carried to other areas of a patient, the enzymes may break down undamaged tissue and cause other complications.

These limitations and others may be addressed by the therapy system 100, which can provide negative-pressure therapy, instillation therapy, disruption of debris, and application of an antibacterial or antimicrobial agent. In some embodiments, the therapy system 100 can provide mechanical movement at a surface of the tissue site in combination with cyclic delivery and dwell of topical solutions to help solubilize debris. For example, a negative-pressure source may be fluidly coupled to a tissue site to provide negative pressure to the tissue site for negative-pressure therapy. In some embodiments, a fluid source may be fluidly coupled to a tissue site to provide therapeutic fluid to the tissue site for instillation therapy. In some embodiments, the therapy system 100 may include a contact layer positioned adjacent to a tissue site that may be used with negative-pressure therapy, instillation therapy, or both to disrupt areas of a tissue site having debris. Following the disruption of the debris, negative-pressure therapy, instillation therapy, and other processes may be used to remove the debris from a tissue site.

The dressing may also include a coating having an antibacterial or antimicrobial agent. In some embodiments, the therapy system 100 may be used in conjunction with other tissue removal and debridement techniques. For example, the therapy system 100 may be used prior to enzymatic debridement to soften the debris. In another example, mechanical debridement may be used to remove a portion of the debris at the tissue site, and the therapy system 100 may then be used to remove the remaining debris while reducing the risk of trauma to the tissue site.

Figure 2:
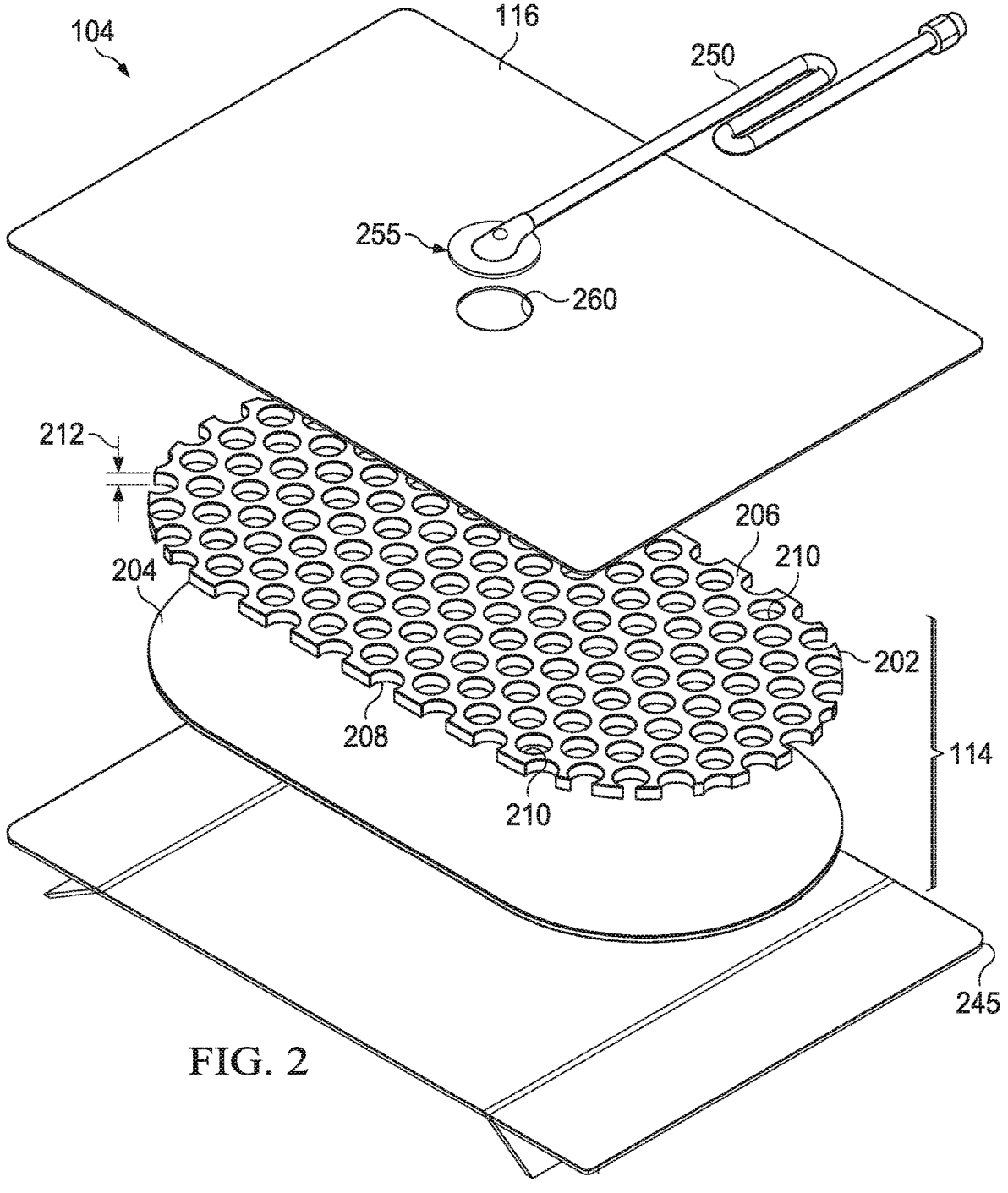
FIG. 2 is an assembly view of an example of a dressing of FIG. 1, illustrating additional details that may be associated with some embodiments in which a tissue interface comprises multiple layers.

FIG. 2 is an assembly view of an example of the dressing 104 of FIG. 1, illustrating additional details that may be associated with some embodiments in which the tissue interface 114 comprises multiple layers. In some embodiments, the tissue interface 114 can include a debridement tool or contact layer 202 and a film layer 204. The contact layer 202 may have a first surface 206, a second surface 208, and a plurality of through-holes 210 extending through the contact layer 202 from the first surface 206 to the second surface 208. The film layer 204 may be disposed adjacent to the second surface 208 of the contact layer 202. In some embodiments, the film layer 204 can be coupled to the second surface 208 of the contact layer 202.

The contact layer 202 may have a substantially uniform thickness 212. In some embodiments, the thickness 212 may be between about 7 mm and about 15 mm. In other embodiments, the thickness 212 may be thinner or thicker than the stated range as needed for the tissue site. In a preferred embodiment, the thickness 212 may be about 8 mm. In some embodiments, individual portions of the contact layer 202 may have a minimal tolerance from the thickness 212. In some embodiments, the thickness 212 may have a tolerance of about 2 mm. In some embodiments, the thickness 212 may be between about 6 mm and about 10 mm. The contact layer 202 may be flexible so that the contact layer 202 can be contoured to a surface of the tissue site.

In some embodiments, the contact layer 202 may be formed from thermoplastic elastomers (TPE), such as styrene ethylene butylene styrene (SEBS) copolymers, or thermoplastic polyurethane (TPU). The contact layer 202 may be formed by combining sheets of TPE or TPU. In some embodiments, the sheets of TPE or TPU may be bonded, welded, adhered, or otherwise coupled to one another. For example, in some embodiments, the sheets of TPE or TPU may be welded using radiant heat, radio-frequency welding, or laser welding. Supracor, Inc., Hexacor, Ltd., Hexcel Corp., and Econocorp, Inc. may produce suitable TPE or TPU sheets for the formation of the contact layer 202. In some embodiments, sheets of TPE or TPU having a thickness between about 0.2 mm and about 2.0 mm may be used to form a structure having the thickness 212. In some embodiments, the contact layer 202 may be formed from a 3D textile, also referred to as a spacer fabric. Suitable 3D textiles may be produced by Heathcoat Fabrics, Ltd., Baltex, and Mueller Textil Group. The contact layer 202 can also be formed from polyurethane, silicone, polyvinyl alcohol, and metals, such as copper, tin, silver or other beneficial metals.

In some embodiments, the contact layer 202 may be formed from a foam. For example, cellular foam, open-cell foam, reticulated foam, or porous tissue collections, may be used to form the contact layer 202. In some embodiments, the contact layer 202 may be formed of V.A.C.® GRANUFOAM™ Dressing, grey foam, or Zotefoam. Grey foam may be a polyester polyurethane foam having about 60 pores per inch (ppi). Zotefoam may be a closed-cell cross-linked polyolefin foam. In one non-limiting example, the contact layer 202 may be an open-cell, reticulated polyurethane foam such as V.A.C.® GRANUFOAM™ Dressing available from Kinetic Concepts, Inc. of San Antonio, Texas; in other embodiments, the contact layer 202 may be an open-cell, reticulated polyurethane foam such as a V.A.C. VERAFLO™ dressing, also available from Kinetic Concepts, Inc., of San Antonio, Texas.

In some embodiments, the contact layer 202 may be formed from a foam that is mechanically or chemically compressed to increase the density of the foam at ambient pressure. A foam that is mechanically or chemically compressed may be referred to as a compressed foam. A compressed foam may be characterized by a firmness factor (FF) that is defined as a ratio of the density of a foam in a compressed state to the density of the same foam in an uncompressed state. For example, a firmness factor (FF) of 5 may refer to a compressed foam having a density at ambient pressure that is five times greater than a density of the same foam in an uncompressed state at ambient pressure. Mechanically or chemically compressing a foam may reduce a thickness of the foam at ambient pressure when compared to the same foam that has not been compressed. Reducing a thickness of a foam by mechanical or chemical compression may increase a density of the foam, which may increase the firmness factor (FF) of the foam. Increasing the firmness factor (FF) of a foam may increase a stiffness of the foam in a direction that is parallel to a thickness of the foam. For example, increasing a firmness factor (FF) of the contact layer 202 may increase a stiffness of the contact layer 202 in a direction that is parallel to the thickness 212 of the contact layer 202. In some embodiments, a compressed foam may be a compressed V.A.C.® GRANUFOAM™ Dressing. V.A.C.® GRANUFOAM™ Dressing may have a density of about 0.03 grams per centimeter$^3$ (g/cm$^3$) in its uncompressed state. If the V.A.C.® GRANUFOAM™ Dressing is compressed to have a firmness factor (FF) of 5, the V.A.C.® GRANUFOAM™ Dressing may be compressed until the density of the V.A.C.® GRANUFOAM™ Dressing is about 0.15 g/cm$^3$. V.A.C. VERAFLO™ dressing may also be compressed to form a compressed foam having a firmness factor (FF) up to 5. In some embodiments, the contact layer 202 may have a thickness between about 4 mm to about 15 mm, and more specifically, about 8 mm at ambient pressure. In an exemplary embodiment, if the thickness 212 of the contact layer is about 8 mm, and the contact layer 202 is positioned within the sealed environment and subjected to negative pressure of about −115 mmHg to about −135 mm Hg, the thickness 212 of the contact layer 202 may be between about 1 mm and about 5 mm and, generally, greater than about 3 mm.

A compressed foam may also be referred to as a felted foam. As with a compressed foam, a felted foam undergoes a thermoforming process to permanently compress the foam to increase the density of the foam. A felted foam may also be compared to other felted foams or compressed foams by comparing the firmness factor of the felted foam to the firmness factor of other compressed or uncompressed foams. Generally a compressed or felted foam may have a firmness factor greater than 1.

The firmness factor (FF) may also be used to compare compressed foam materials with non-foam materials. For example, a Supracor® material may have a firmness factor (FF) that allows Supracor® to be compared to compressed foams. In some embodiments, the firmness factor (FF) for a non-foam material may represent that the non-foam material has a stiffness that is equivalent to a stiffness of a compressed foam having the same firmness factor. For example, if a contact layer is formed from Supracor®, as illustrated in Table 1 below, the contact layer may have a stiffness that is about the same as the stiffness of a compressed V.A.C. GRANUFOAM™ Dressing material having a firmness factor (FF) of 3.

Generally, if a compressed foam is subjected to negative pressure, the compressed foam exhibits less deformation than a similar uncompressed foam. If the contact layer 202 is formed of a compressed foam, the thickness 212 of the contact layer 202 may deform less than if the contact layer 202 is formed of a comparable uncompressed foam. The decrease in deformation may be caused by the increased stiffness as reflected by the firmness factor (FF). If subjected to the stress of negative pressure, the contact layer 202 that is formed of compressed foam may flatten less than the contact layer 202 that is formed from uncompressed foam. Consequently, if negative pressure is applied to the contact layer 202, the stiffness of the contact layer 202 in the direction parallel to the thickness 212 of the contact layer 202 allows the contact layer 202 to be more compliant or compressible in other directions, e.g., a direction perpendicular to the thickness 212. The foam material used to form a compressed foam may be either hydrophobic or hydrophilic. The foam material used to form a compressed foam may also be either reticulated or un-reticulated. The pore size of a foam material may vary according to needs of the contact layer 202 and the amount of compression of the foam. For example, in some embodiments, an uncompressed foam may have pore sizes in a range of about 400 microns to about 600 microns. If the same foam is compressed, the pore sizes may be smaller than when the foam is in its uncompressed state.

The film layer 204 may be a film of a material having antimicrobial and/or antibacterial properties. For example, the film layer 204 can be formed from a mixture containing silver, citric acid, acetic acid, or a combination thereof. In some embodiments, the film layer 204 can be a coating of silver, a film of citric acid, or a film of acetic acid. For example, the contact layer 202 may be an open-cell reticulated foam having a thin layer of silver coated onto the foam to form the film layer 204. The reticulated, open-cell structure of the foam may be maintained after the coating process. For example, following the application of a silver coating, the foam may have pore sizes in the range of about 400 microns to about 600 microns. In some embodiments, the silver coating of the film layer 204 may have a thickness of about 1 micron to about 10 microns and, in particular, about 3 microns. In some embodiments, the coating of silver may extend through the open-cell reticulated foam of the contact layer 202 so that substantially all surfaces of the contact layer 202 may be coated. In other embodiments, the silver coating of the film layer 204 may only be applied to a portion of the contact layer 202 or to the second surface 208 of the contact layer 202. The silver coating may be 99.9% pure metallic silver that is bonded to the contact layer 202. In some embodiments, the contact layer 202 may be felted or un-felted V.A.C.® GRANUFOAM SILVER™ Dressing available from KCI, Inc.

In other embodiments, the film layer 204 can be formed from acetic acid. For example, the film layer 204 can be a 100 millimolar ("mM") acetic acid. In an exemplary formulation, 2.0 grams of collagen and oxidized regenerated cellulose ("ORC") can be placed in 200 milliliters ("mL") of 0.05 molarity ("M") acetic acid. The collagen/ORC can absorb or swell with the acetic acid for about 5 minutes. Mixing of the collagen/ORC and the acetic acid can be followed by the addition of glycerol. The glycerol can be added by drop and mixed until a concentration of the solution ("v/v") is approximately 300 microliters ("µL") of glycerol per 100 mL of acetic acid or 0.3% v/v. In the example embodiment, about 600 µL of glycerol were added to the 200 mL of acetic acid. The resulting solution can be mixed and placed in a vacuum chamber to draw out gas bubbles from the solution.

In some embodiments, the solution can be placed into trays in about 20 mL quantities and incubated at 37° C. to produce a film having a thickness between about 100 microns and about 500 microns. The film layer 204 can be coated onto the second surface 208 of the contact layer 202. For example, the second surface 208 of the contact layer 202 can be placed into a tray having the solution while the solution cures into the film layer 204. In other embodiments, the acetic acid can be produced in the ratios described to produce sheets of film. The sheets can be positioned over the contact layer 202 and placed in contact with the contact layer 202. The natural tackiness of the acetic acid sheet can couple the sheet to the contact layer 202. For example, the tackiness of the acetic acid sheet of the film layer 204 can bond the sheet to the contact layer 202. In some embodiments, the film layer 204 can cover the through-holes 210 of the contact layer 202. In other embodiments, the film layer 204 can be removed from the contact layer 202 at the plurality of through-holes 210, leaving the film layer 204 coating the walls 302 of the second surface 208. In still other embodiments, the through-holes 210 of the contact layer 202 can be formed after the film layer 204 is coupled to the contact layer 202.

In other embodiments, the film layer 204 can be formed from citric acid. For example, the film layer 204 can be a 100 millimolar ("mM") citric acid. For example, citric acid powder can be dissolved into water or other similar solution. Glycerol can be titrated into the citric acid as described above to produce sheets of the citric acid film. The process produced an exemplary 100 mM citric acid solution and an exemplary 200 mM citric acid solution. The 100 mM citric acid solution had a formula weight of about 129.12 Daltons, a volume of 110 mL, and a mass of about 2.1 grams. The film layer 204 can be coated onto the second surface 208 of the contact layer 202. In some embodiments, the film layer 204 can cover the through-holes 210 of the contact layer 202. In other embodiments, the film layer 204 can be removed from the contact layer 202 at the plurality of through-holes 210.

As illustrated in the example of FIG. 2, in some embodiments, the dressing 104 may include a release liner 245 to protect an optional adhesive on a portion of the cover 116 prior to use. The release liner 245 may also provide stiffness to assist with, for example, deployment of the dressing 104. The release liner 245 may be, for example, a casting paper, a film, or polyethylene. Further, in some embodiments, the release liner 245 may be a polyester material such as polyethylene terephthalate (PET), or similar polar semi-crystalline polymer. The use of a polar semi-crystalline polymer for the release liner 245 may substantially preclude wrinkling or other deformation of the dressing 104. For example, the polar semi-crystalline polymer may be highly orientated and resistant to softening, swelling, or other deformation that may occur when brought into contact with components of the dressing 104, or when subjected to temperature or environmental variations, or sterilization. Further, a release agent may be disposed on a side of the release liner 245 that is configured to contact the tissue interface 114. For example, the release agent may be a silicone coating and may have a release factor suitable to facilitate removal of the release liner 245 by hand and without damaging or deforming the dressing 104. In some embodiments, the release agent may be a fluorocarbon or a fluorosilicone, for example. In other embodiments, the release liner 245 may be uncoated or otherwise used without a release agent.

FIG. 2 also illustrates one example of a fluid conductor 250 and a dressing interface 255. As shown in the example of FIG. 2, the fluid conductor 250 may be a flexible tube, which can be fluidly coupled on one end to the dressing interface 255. The dressing interface 255 may be an elbow connector, as shown in the example of FIG. 2, which can be placed over an aperture 260 in the cover 116 to provide a fluid path between the fluid conductor 250 and the tissue interface 114.

Figure 3:
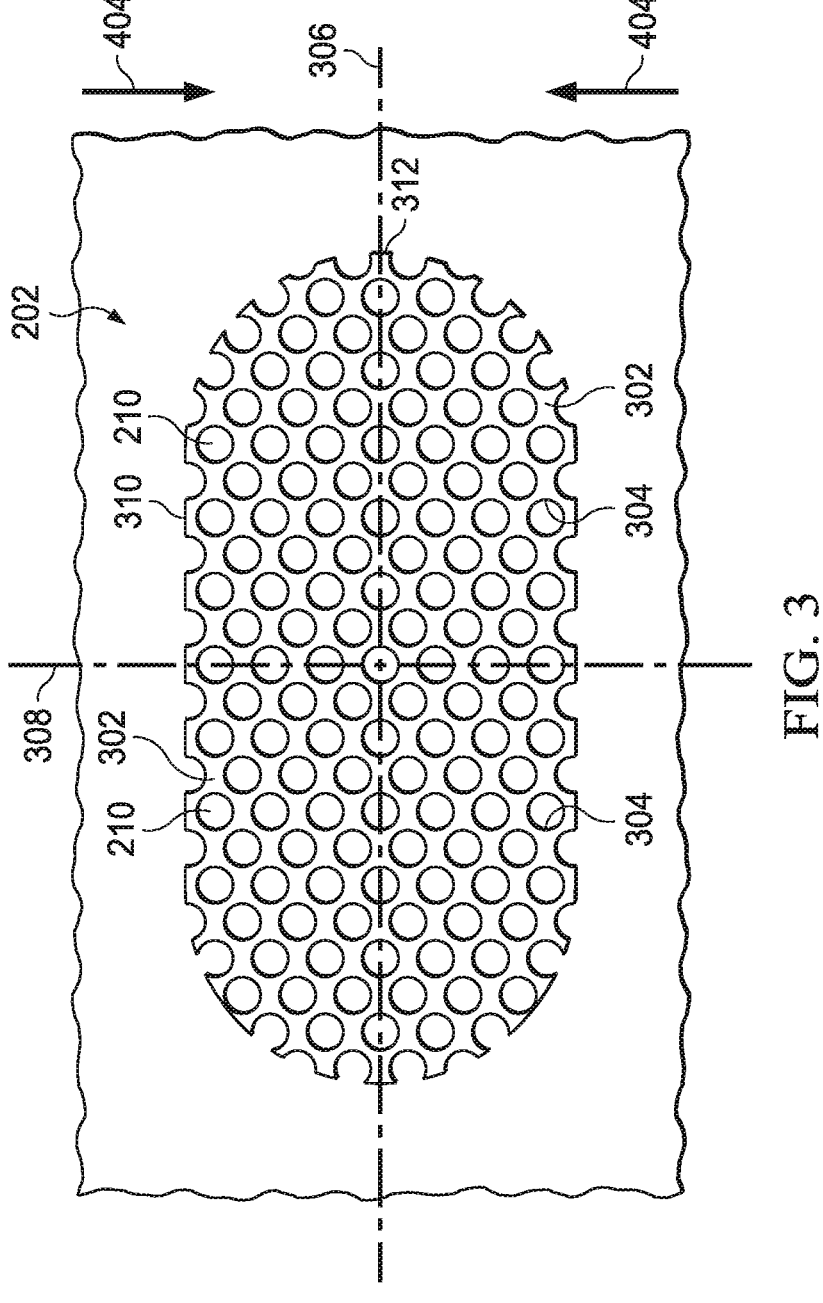
FIG. 3 is a plan view, illustrating additional details that may be associated with some embodiments of a contact layer.

FIG. 3 is a plan view, illustrating additional details that may be associated with some embodiments of the contact layer 202. The contact layer 202 may include a plurality of through-holes 210 or other perforations extending through the contact layer 202 to form walls 302. In some embodiments, an exterior surface of the walls 302 may be parallel to sides of the contact layer 202. In other embodiments, an interior surface of the walls 302 may be generally perpendicular to the second surface 208 and the first surface 206 of the contact layer 202. Generally, the exterior surface or surfaces of the walls 302 may be coincident with the second surface 208 and the first surface 206. The interior surface or surfaces of the walls 302 may form a perimeter 304 of each through-hole 210 and may connect the second surface 208 to the first surface 206. In some embodiments, the through-holes 210 may have a circular shape as shown. In some embodiments, the through-holes 210 may have diameters between about 5 mm and about 20 mm, and in some embodiments, the diameters of the through-holes 210 may be about 10 mm. The through-holes 210 may have a depth that is about equal to the thickness 212 of the contact layer 202. For example, the through-holes 210 may have a depth between about 6 mm to about 10 mm, and more specifically, about 8 mm at ambient pressure.

In some embodiments, the contact layer 202 may have a first orientation line 306 and a second orientation line 308 that is perpendicular to the first orientation line 306. The first orientation line 306 and the second orientation line 308 may be lines of symmetry of the contact layer 202. A line of symmetry may be, for example, an imaginary line across the second surface 208 or the first surface 206 of the contact layer 202 defining a fold line such that if the contact layer 202 is folded on the line of symmetry, the through-holes 210 and walls 302 would be coincidentally aligned. Generally, the first orientation line 306 and the second orientation line 308 aid in the description of the contact layer 202. In some embodiments, the first orientation line 306 and the second orientation line 308 may be used to refer to the desired directions of contraction of the contact layer 202. For example, the desired direction of contraction may be parallel to the second orientation line 308 and perpendicular to the first orientation line 306. In other embodiments, the desired direction of contraction may be parallel to the first orientation line 306 and perpendicular to the second orientation line 308. In still other embodiments, the desired direction of contraction may be at a non-perpendicular angle to both the first orientation line 306 and the second orientation line 308. In other embodiments, the contact layer 202 may not have a desired direction of contraction. Generally, the contact layer 202 may be placed at the tissue site so that the second orientation line 308 extends across debris located at the tissue site. Although the contact layer 202 is shown as having a generally rectangular shape including longitudinal edges 310 and circular edges 312, the contact layer 202 may have other shapes. For example, the contact layer 202 may have a diamond, square, or circular shape. In some embodiments, the shape of the contact layer 202 may be selected to accommodate the type of tissue site being treated. For example, the contact layer 202 may have an oval or circular shape to accommodate an oval or circular tissue site. In some embodiments, the first orientation line 306 may be parallel to the longitudinal edges 310.

Figure 4:
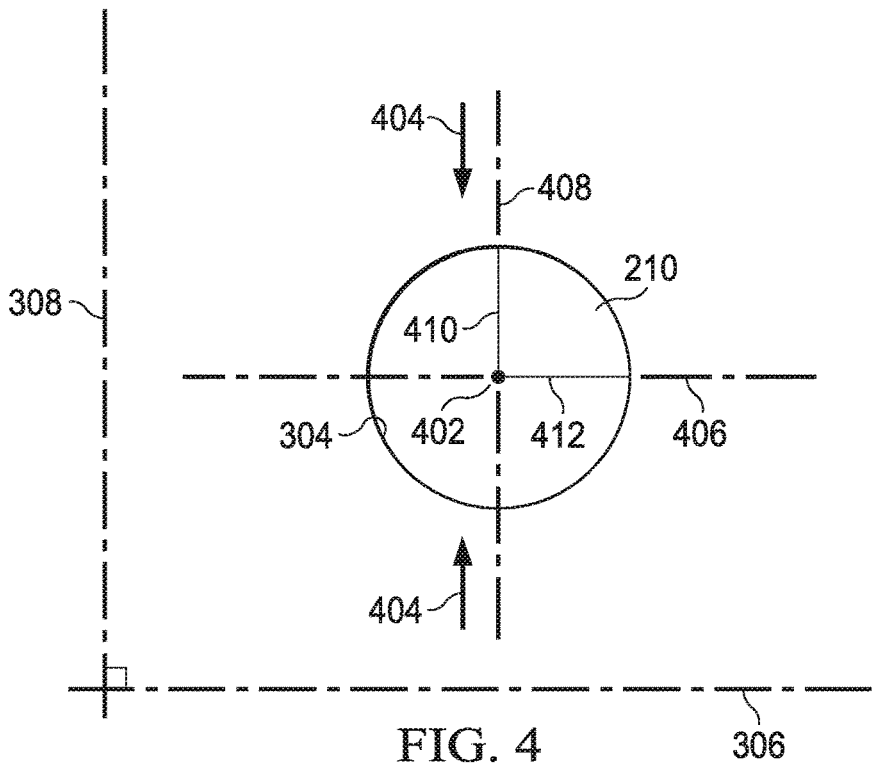
FIG. 4 is a plan view illustrating additional details that may be associated with some embodiments of a hole of the contact layer of FIG. 2.

FIG. 4 is a plan view illustrating additional details that may be associated with some embodiments of the through-hole 210 of the contact layer 202 of FIG. 3. In FIG. 4, a single through-hole 210 having a circular shape is shown. The through-hole 210 may include a center 402 and the perimeter 304. The through-hole 210 may have a perforation shape factor (PSF). The perforation shape factor (PSF) may represent an orientation of the through-hole 210 relative to the first orientation line 306 and the second orientation line 308. Generally, the perforation shape factor (PSF) is a ratio of ½ a maximum length of the through-hole 210 that is parallel to the desired direction of contraction to ½ a maximum length of the through-hole 210 that is perpendicular to the desired direction of contraction. For descriptive purposes, the desired direction of contraction is parallel to the second orientation line 308. The desired direction of contraction may be indicated by a lateral force 404. For reference, the through-hole 210 may have an X-axis 406 extending through the center 402 parallel to the first orientation line 306, and a Y-axis 408 extending through the center 402 parallel to the second orientation line 308. The perforation shape factor (PSF) of the through-hole 210 may be defined as a ratio of a line segment 410 on the Y-axis 408 extending from the center 402 to the perimeter 304 of the through-hole 210, to a line segment 412 on the X-axis 406 extending from the center 402 to the perimeter 304 of the through-hole 210. If a length of the line segment 410 is 2.5 mm and the length of the line segment 412 is 2.5 mm, the perforation shape factor (PSF) would be 1. In other embodiments, the through-holes 210 may have other shapes and orientations, for example, oval, hexagonal, square, triangular, or amorphous or irregular and be oriented relative to the first orientation line 306 and the second orientation line 308 so that the perforation shape factor (PSF) may range from about 0.5 to about 1.10.

Figure 5:
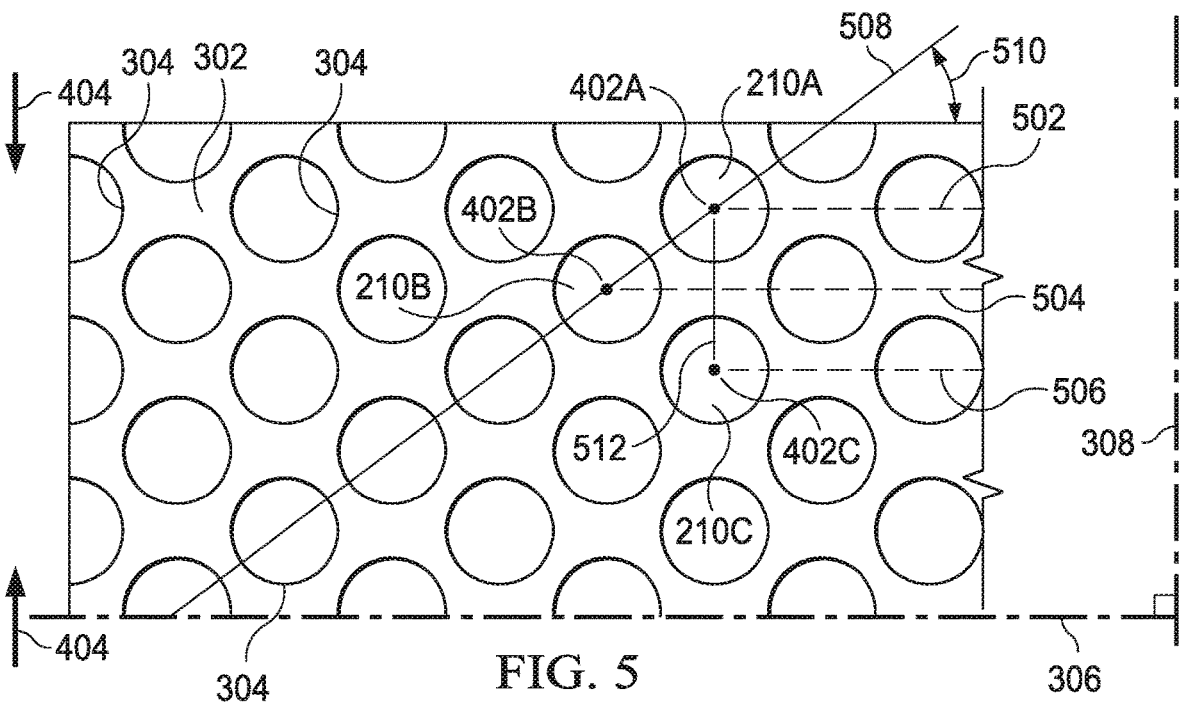
FIG. 5 is a plan view illustrating additional details of a portion of the contact layer of FIG. 2.

FIG. 5 is a plan view illustrating additional details of a portion of the contact layer 202 of FIG. 3. The contact layer 202 may include the plurality of through-holes 210 aligned in parallel rows to form an array. The array of through-holes 210 may include a first row 502 of the through-holes 210, a second row 504 of the through-holes 210, and a third row 506 of the through-holes 210. In some embodiments, a width of the wall 302 between the perimeters 304 of adjacent the through-holes 210 in a row, such as the first row 502, may be about 5 mm. The centers 402 of the through-holes 210 in adjacent rows, for example, the first row 502 and the second row 504, may be characterized by being offset from the second orientation line 308 along the first orientation line 306. In some embodiments, a line connecting the centers of adjacent rows may form a strut angle (SA) with the first orientation line 306. For example, a first through-hole 210A in the first row 502 may have a center 402A, and a second through-hole 210B in the second row 504 may have a center 402B. A strut line 508 may connect the center 402A with the center 402B. The strut line 508 may form an angle 510 with the first orientation line 306. The angle 510 may be the strut angle (SA) of the contact layer 202. In some embodiments, the strut angle (SA) may be less than about 90°. In other embodiments, the strut angle (SA) may be between about 30° and about 70° relative to the first orientation line 306. In other embodiments, the strut angle (SA) may be about 66° from the first orientation line 306. Generally, as the strut angle (SA) decreases, a stiffness of the contact layer 202 in a direction parallel to the first orientation line 306 may increase. Increasing the stiffness of the contact layer 202 parallel to the first orientation line 306 may increase the compressibility of the contact layer 202 perpendicular to the first orientation line 306. Consequently, if negative pressure is applied to the contact layer 202, the contact layer 202 may be more compliant or compressible in a direction perpendicular to the first orientation line 306. By increasing the compressibility of the contact layer 202 in a direction perpendicular to the first orientation line 306, the contact layer 202 may collapse to apply the lateral force 404 to the tissue site described in more detail below.

In some embodiments, the centers 402 of the through-holes 210 in alternating rows, for example, the center 402A of the first through-hole 210A in the first row 502 and a center 402C of a through-hole 210C in the third row 506, may be spaced from each other parallel to the second orientation line 308 by a length 512. In some embodiments, the length 512 may be greater than an effective diameter of the through-hole 210. If the centers 402 of through-holes 210 in alternating rows are separated by the length 512, the exterior surface of the walls 302 parallel to the first orientation line 306 may be considered continuous. Generally, the exterior surface of the walls 302 may be continuous if the exterior surface of the walls 302 do not have any discontinuities or breaks between through-holes 210. In some embodiments, the length 512 may be between about 7 mm and about 25 mm.

Regardless of the shape of the through-holes 210, the through-holes 210 in the contact layer 202 may leave void spaces in the contact layer 202 and on the second surface 208 and the first surface 206 of the contact layer 202 so that only the exterior surface of the walls 302 of the contact layer 202 remain with a surface available to contact the tissue site. It may be desirable to minimize the exterior surface of the walls 302 so that the through-holes 210 may collapse, causing the contact layer 202 to collapse and generate the lateral force 404 in a direction perpendicular to the first orientation line 306. However, it may also be desirable not to minimize the exterior surface of the walls 302 so much that the contact layer 202 becomes too fragile for sustaining the application of a negative pressure. The void space percentage (VS) of the through-holes 210 may be equal to the percentage of the volume or surface area of the void spaces of the second surface 208 created by the through-holes 210 to the total volume or surface area of the second surface 208 of the contact layer 202. In some embodiments, the void space percentage (VS) may be between about 40% and about 75%. In other embodiments, the void space percentage (VS) may be about 55%. The organization of the through-holes 210 can also impact the void space percentage (VS), influencing the total surface area of the contact layer 202 that may contact the tissue site. In some embodiments, the longitudinal edge 310 and the circular edge 312 of the contact layer 202 may be discontinuous. An edge may be discontinuous where the through-holes 210 overlap an edge causing the edge to have a non-linear profile. A discontinuous edge may reduce the disruption of keratinocyte migration and enhance re-epithelialization while negative pressure is applied to the dressing 104.

In other embodiments, the through-holes 210 of the contact layer 202 may have a depth that is less than the thickness 212 of the contact layer 202. For example, the through-holes 210 may be blind holes formed in the second surface 208 of the contact layer 202. The through-holes 210 may leave void spaces in the contact layer 202 on the second surface 208 so that only the exterior surface of the walls 302 of the contact layer 202 on the second surface 208 remain with a surface available to contact the tissue site at ambient pressure. If a depth of the through-holes 210 extending from the second surface 208 toward the first surface 206 is less than the thickness 212, the void space percentage (VS) of the first surface 206 may be zero, while the void space percentage (VS) of the second surface 208 is greater than zero, for example 55%.

In some embodiments, the through-holes 210 may be formed during molding of the contact layer 202. In other embodiments, the through-holes 210 may be formed by cutting, melting, drilling, or vaporizing the contact layer 202 after the contact layer 202 is formed. For example, the through-holes 210 may be formed in the contact layer 202 by laser cutting the compressed foam of the contact layer 202. In some embodiments, the through-holes 210 may be formed so that the interior surfaces of the walls 302 of the through-holes 210 are parallel to the thickness 212. In other embodiments, the through-holes 210 may be formed so that the interior surfaces of the walls 302 of the through-holes 210 form a non-perpendicular angle with the second surface 208. In still other embodiments, the interior surfaces of the walls 302 of the through-holes 210 may taper toward the center 402 of the through-holes 210 to form conical, pyramidal, or other irregular through-hole shapes. If the interior surfaces of the walls 302 of the through-holes 210 taper, the through-holes 210 may have a height less than the thickness 212 of the contact layer 202.

In some embodiments, formation of the through-holes 210 may thermoform the material of the contact layer 202, for example a compressed foam or a felted foam, causing the interior surface of the walls 302 extending between the second surface 208 and the first surface 206 to be smooth. As used herein, smoothness may refer to the formation of the through-holes 210 that causes the interior surface of the walls 302 that extends between the second surface 208 and the first surface 206 to be substantially free of pores if compared to an uncut portion of the contact layer 202. For example, laser-cutting the through-holes 210 into the contact layer 202, may plastically deform the material of the contact layer 202, closing any pores on the interior surfaces of the walls 302 that extend between the second surface 208 and the first surface 206. In some embodiments, a smooth interior surface of the walls 302 may limit or otherwise inhibit ingrowth of tissue into the contact layer 202 through the through-holes 210. In other embodiments, the smooth interior surfaces of the walls 302 may be formed by a smooth material or a smooth coating.

In some embodiments, an effective diameter of the through-holes 210 may be selected to permit flow of particulates through the through-holes 210. In some embodiments, the diameter of the through-holes 210 may be selected based on the size of the solubilized debris to be lifted from the tissue site. Larger through-holes 210 may allow larger debris to pass through the contact layer 202, and smaller through-holes 210 may allow smaller debris to pass through the contact layer 202 while blocking debris larger than the through-holes. In some embodiments, successive applications of the dressing 104 can use contact layers 202 having successively smaller diameters of the through-holes 210 as the size of the solubilized debris in the tissue site decreases. Sequentially decreasing diameters of the through-holes 210 may also aid in fine tuning a level of tissue disruption to the debris during the treatment of the tissue site. The diameter of the through-holes 210 can also influence fluid movement in the contact layer 202 and the dressing 104. For example, the contact layer 202 can channel fluid in the dressing 104 toward the through-holes 210 to aid in the disruption of the debris on the tissue site. Variation of the diameters of the through-holes 210 can vary how fluid is moved through the dressing 104 with respect to both the removal of fluid and the application of negative pressure. In some embodiments, the effective diameter of the through-holes 210 is between about 5 mm and about 20 mm and, more specifically, about 10 mm.

An effective diameter of a non-circular area is defined as a diameter of a circular area having the same surface area as the non-circular area. In some embodiments, each through-hole 210 may have an effective diameter of about 3.5 mm. In other embodiments, each through-hole 210 may have an effective diameter between about 5 mm and about 20 mm. The effective diameter of the through-holes 210 should be distinguished from the porosity of the material forming the walls 302 of the contact layer 202. Generally, an effective diameter of the through-holes 210 is an order of magnitude larger than the effective diameter of the pores of a material forming the contact layer 202. For example, the effective diameter of the through-holes 210 may be larger than about 1 mm, while the walls 302 may be formed from V.A.C.® GRANUFOAM™ Dressing having a pore size less than about 600 microns. In some embodiments, the pores of the walls 302 may not create openings that extend all the way through the material. Generally, the through-holes 210 do not include pores formed by the foam formation process, and the through-holes 210 may have an average effective diameter that is greater than ten times an average effective diameter of pores of a material.

Referring now to both FIGS. 3 and 5, the through-holes 210 may form a pattern depending on the geometry of the through-holes 210 and the alignment of the through-holes 210 between adjacent and alternating rows in the contact layer 202 with respect to the first orientation line 306. If the contact layer 202 is subjected to negative pressure, the through-holes 210 of the contact layer 202 may contract. As used herein, contraction can refer to both vertical compression of a body parallel to a thickness of the body, such as the contact layer 202, and lateral compression of a body perpendicular to a thickness of the body, such as the contact layer 202. In some embodiments the void space percentage (VS), the perforation shape factor (PSF), and the strut angle (SA) may cause the contact layer 202 to contract along the second orientation line 308 perpendicular to the first orientation line 306 as shown in more detail in FIG. 6.

Figure 6:
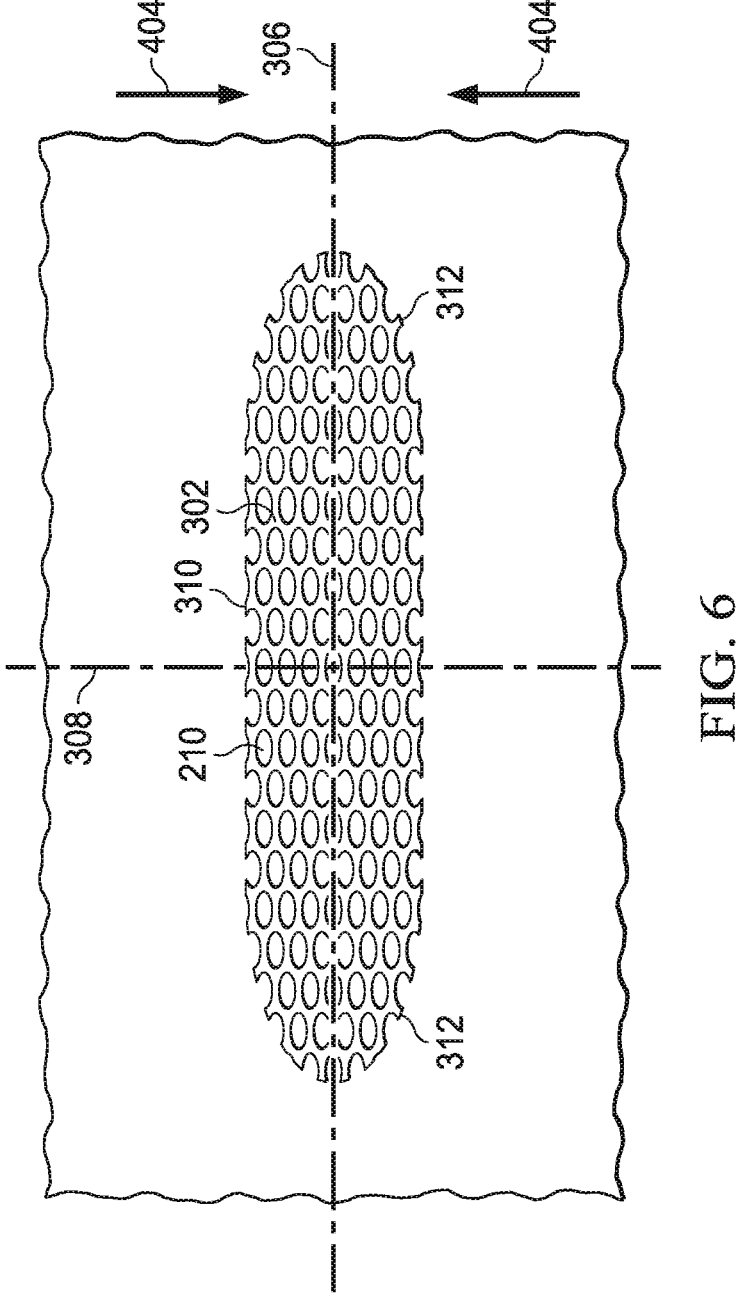
FIG. 6 is a plan view illustrating additional details of the contact layer of FIG. 3 in a contracted state.

FIG. 6 is a plan view illustrating additional details of the contact layer 202 of FIG. 3 in a contracted state. If the contact layer 202 is positioned on the tissue site, the contact layer 202 may generate the lateral force 404 along the second orientation line 308, contracting the contact layer 202, as shown in more detail in FIG. 6. The lateral force 404 may be optimized by adjusting the factors described above as set forth in Table 1 below. In some embodiments, the through-holes 210 may be circular, have a strut angle (SA) of approximately 37°, a void space percentage (VS) of about 54%, a firmness factor (FF) of about 5, a perforation shape factor (PSF) of about 1, and a diameter of about 5 mm. If the contact layer 202 is subjected to a negative pressure of about −125 mmHg, the contact layer 202 asserts the lateral force 404 of approximately 11.9 N. If the diameter of the through-holes 210 of the contact layer 202 is increased to about 20 mm, the void space percentage (VS) changed to about 52%, the strut angle (SA) changed to about 52°, and the perforation shape factor (PSF) and the firmness factor (FF) remain the same, the lateral force 404 is decreased to about 6.5 N. In other embodiments, the through-holes 210 may be hexagonal, have a strut angle (SA) of approximately 66°, a void space percentage (VS) of about 55%, a firmness factor (FF) of about 5, a perforation shape factor (PSF) of about 1.07, and an effective diameter of about 5 mm. If the contact layer 202 is subjected to a negative pressure of about −125 mmHg, the lateral force 404 asserted by the contact layer 202 is about 13.3 N. If the effective diameter of the through-holes 210 of the contact layer 202 is increased to 10 mm, the lateral force 404 is decreased to about 7.5 N.

Referring to FIG. 6, the contact layer 202 is in the second position, or contracted position, as indicated by the lateral force 404. In operation, negative pressure is supplied to the sealed environment with the negative-pressure source 102. In response to the supply of negative pressure, the contact layer 202 contracts from the relaxed position illustrated in FIG. 3 to the contracted position illustrated in FIG. 6. In some embodiments, the thickness 212 of the contact layer 202 remains substantially the same. When the negative pressure is removed, for example, by venting the negative pressure, the contact layer 202 expands back to the relaxed position. If the contact layer 202 is cycled between the contracted and relaxed positions of FIG. 6 and FIG. 3, respectively, the second surface 208 of the contact layer 202 may disrupt the debris on the tissue site by rubbing the debris from the tissue site. The edges of the through-holes 210 formed by the second surface 208 and the interior surfaces or transverse surfaces of the walls 302 can form cutting edges that can disrupt the debris in the tissue site, allowing the debris to exit through the through-holes 210. In some embodiments, the cutting edges are defined by the perimeter 304 where each through-hole 210 intersects the second surface 208.

In some embodiments, the material, the void space percentage (VS), the firmness factor, the strut angle, the hole shape, the perforation shape factor (PSF), and the hole diameter may be selected to increase compression or collapse of the contact layer 202 in a lateral direction, as shown by the lateral force 404, by forming weaker walls 302. Conversely, the factors may be selected to decrease compression or collapse of the contact layer 202 in a lateral direction, as shown by the lateral force 404, by forming stronger walls 302. Similarly, the factors described herein can be selected to decrease or increase the compression or collapse of the contact layer 202 perpendicular to the lateral force 404.

In some embodiments, the therapy system 100 may provide cyclic therapy. Cyclic therapy may alternately apply negative pressure to and vent negative pressure from a sealed space or sealed environment containing the tissue interface 114. In some embodiments, negative pressure may be supplied to the tissue site until the pressure in the sealed environment reaches a predetermined therapy pressure. If negative pressure is supplied to the sealed environment, the debris and the subcutaneous tissue underlying the debris may be drawn into the through-holes 210. In some embodiments, the sealed environment may remain at the therapy pressure for a predetermined therapy period such as, for example, about 10 minutes. In other embodiments, the therapy period may be longer or shorter as needed to supply appropriate negative-pressure therapy to the tissue site.

Following the therapy period, the sealed environment may be vented. For example, the negative-pressure source 102 may fluidly couple the sealed environment to the atmosphere (not shown), allowing the sealed environment to return to ambient pressure. In some embodiments, the negative-pressure source 102 may vent the sealed environment for about 1 minute. In other embodiments, the negative-pressure source 102 may vent the sealed environment for longer or shorter periods. After venting of the sealed environment, the negative-pressure source 102 may be operated to begin another negative-pressure therapy cycle.

In some embodiments, instillation therapy may be combined with negative-pressure therapy. For example, following the therapy period of negative-pressure therapy, the solution source 118 may operate to provide fluid to the sealed environment. In some embodiments, the solution source 118 may provide fluid while the negative-pressure source 102 vents the sealed environment. For example, the positive-pressure source 120 may be configured to move instillation fluid from the solution source 118 to the sealed environment. In some embodiments, the solution source 118 may not have a pump and may operate using a gravity feed system. In other embodiments, the negative-pressure source 102 may not vent the sealed environment. Instead, the negative pressure in the sealed environment is used to draw instillation fluid from the solution source 118 into the sealed environment.

In some embodiments, the solution source 118 may provide a volume of fluid to the sealed environment. In some embodiments, the volume of fluid may be the same as a volume of the sealed environment. In other embodiments, the volume of fluid may be smaller or larger than the sealed environment as needed to appropriately apply instillation therapy. Instilling of the tissue site may raise a pressure in the sealed environment to a pressure greater than the ambient pressure, for example to between about 0 mmHg and about 15 mmHg and, more specifically, about 5 mmHg. In some embodiments, the fluid provided by the solution source 118 may remain in the sealed environment for a dwell time. In some embodiments, the dwell time is about 5 minutes. In other embodiments, the dwell time may be longer or shorter as needed to appropriately administer instillation therapy to the tissue site. For example, the dwell time may be zero.

At the conclusion of the dwell time, the negative-pressure source 102 may be operated to draw the instillation fluid into the container, completing a cycle of therapy. As the instillation fluid is removed from the sealed environment with negative pressure, negative pressure may also be supplied to the sealed environment, starting another cycle of therapy.

Figure 7:
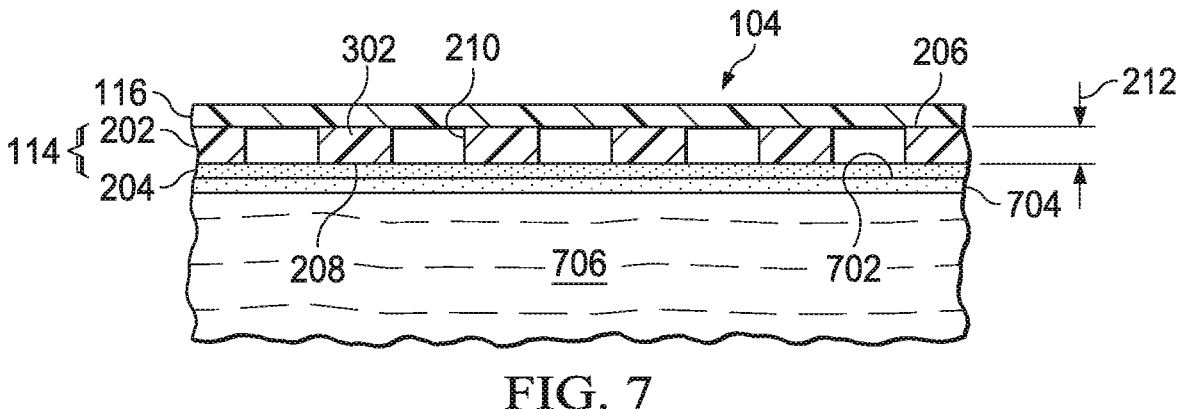
FIG. 7 is a sectional view of a portion of the contact layer of FIG. 3, illustrating additional details that may be associated with some embodiments.

FIG. 7 is a sectional view of a portion of the contact layer 202, illustrating additional details that may be associated with some embodiments. The contact layer 202 and the film layer 204 may be placed at a tissue site 702 having debris 704 covering subcutaneous tissue 706. The film layer 204 may be adjacent to the debris 704 and the contact layer 202 adjacent to the film layer 204. In embodiments having the film layer 204 coupled to or coating the second surface 208 of the contact layer 202, the second surface 208 of the contact layer 202 may be positioned adjacent to the debris 704. The cover 116 may be placed over the contact layer 202 and the film layer 204 to provide a sealed environment for the application of negative-pressure therapy or instillation therapy.

Figure 8:
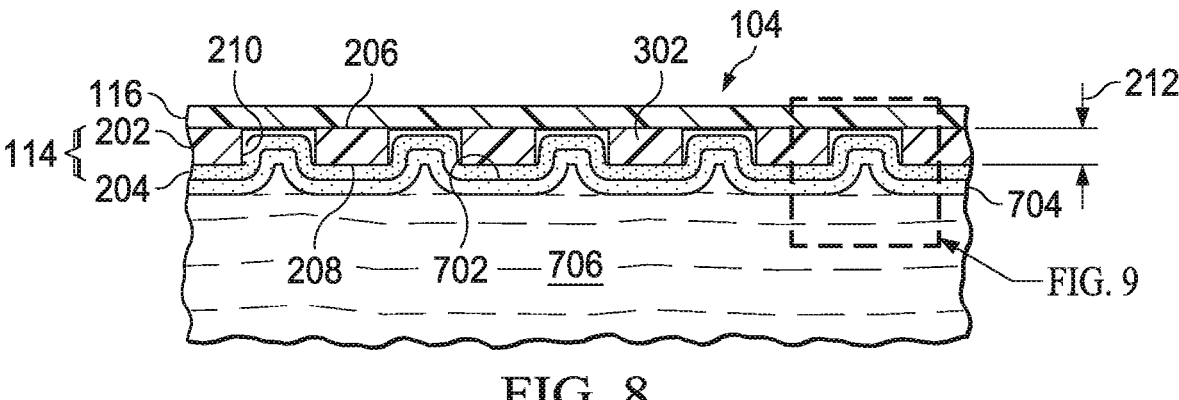
FIG. 8 is a sectional view of a portion of the contact layer of FIG. 3 during negative-pressure therapy, illustrating additional details that may be associated with some embodiments.

FIG. 8 is a sectional view of a portion of the dressing 104 during negative-pressure therapy, illustrating additional details that may be associated with some embodiments. For example, FIG. 8 may illustrate a moment in time where a pressure in the sealed environment may be about 125 mmHg of negative pressure. In some embodiments, the contact layer 202 may be a precompressed or felted foam. In response to the application of negative pressure, the contact layer 202 may not compress. In some embodiments, negative pressure in the sealed environment can generate concentrated stresses in the debris 704 adjacent to the through-holes 210 in the contact layer 202. The concentrated stresses can cause macro-deformations of the debris 704 and the subcutaneous tissue 706 that draws portions of the debris 704 and the subcutaneous tissue 706 into the through-holes 210. Similarly, the film layer 204 can be drawn into the through-holes 210, remaining in contact with the debris 704.

Figure 9:
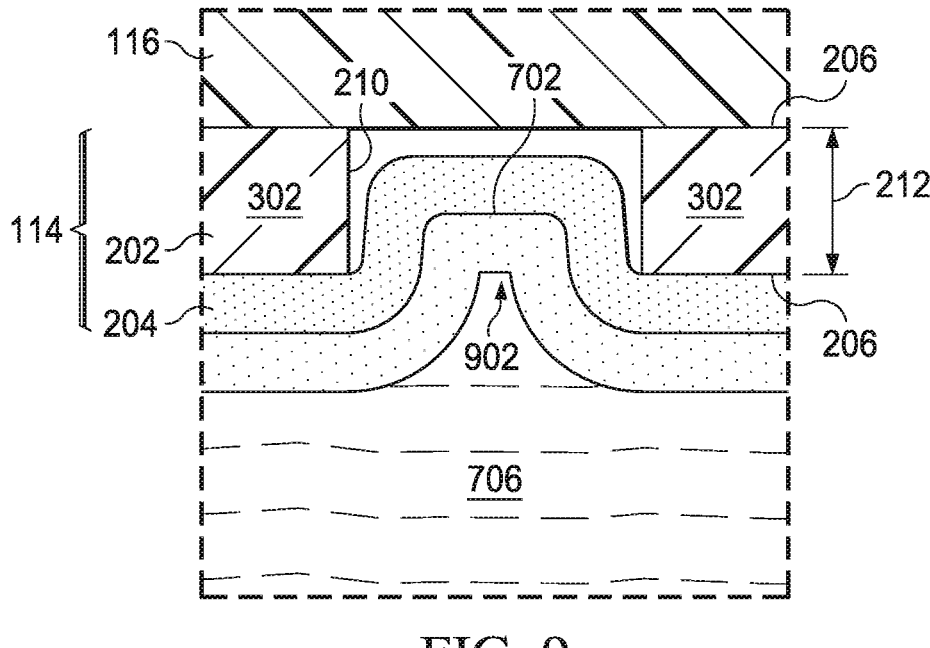
FIG. 9 is a detail view of the contact layer of FIG. 3, illustrating additional details of the operation of the contact layer during negative-pressure therapy.

FIG. 9 is a detail view of the contact layer 202, illustrating additional details of the operation of the contact layer 202 during negative-pressure therapy. The through-holes 210 of the contact layer 202 may create macro-pressure points in portions of the film layer 204, the debris 704, and the subcutaneous tissue 706 that are in contact with the second surface 208 of the contact layer 202, causing tissue puckering and nodules 902 in the film layer 204, the debris 704, and the subcutaneous tissue 706.

A height of the nodules 902 over the surrounding tissue may be selected to maximize disruption of debris 704 and minimize damage to subcutaneous tissue 706 or other desired tissue. Generally, the pressure in the sealed environment can exert a force that is proportional to the area over which the pressure is applied. At the through-holes 210 of the contact layer 202, the force may be concentrated as the resistance to the application of the pressure is less than in the walls 302 of the contact layer 202. In response to the force generated by the pressure at the through-holes 210, the debris and the subcutaneous tissue 706 that forms the nodules 902 may be drawn into and through the through-holes 210 until the force applied by the pressure is equalized by the reactive force of the film layer 204, the debris 704, and the subcutaneous tissue 706. In some embodiments where the negative pressure in the sealed environment may cause tearing, the thickness 212 of the contact layer 202 may be selected to limit the height of the nodules 902 over the surrounding tissue. In some embodiments, the height of the nodules 902 may be limited to a height that is less than the thickness 212 of the contact layer 202. In an exemplary embodiment, the thickness 212 of the contact layer 202 may be about 7 mm. During the application of negative pressure, the height of the nodules 902 may be limited to about 2 mm to about 7 mm. By controlling the height of the nodules 902 by controlling the thickness 212 of the contact layer 202, the aggressiveness of disruption to the debris 704 and tearing can be controlled.

In some embodiments, the height of the nodules 902 can also be controlled by controlling an expected compression of the contact layer 202 during negative-pressure therapy. For example, the contact layer 202 may have a thickness 212 of about 8 mm. If the contact layer 202 is formed from a compressed foam, the firmness factor of the contact layer 202 may be higher; however, the contact layer 202 may still reduce in thickness in response to negative pressure in the sealed environment. In one embodiment, application of negative pressure of between about −50 mmHg and about −350 mmHg, between about −100 mm Hg and about −250 mmHg and, more specifically, about −125 mmHg in the sealed environment may reduce the thickness 212 of the contact layer 202 from about 8 mm to about 3 mm. The height of the nodules 902 may be limited to be no greater than the thickness 212 of the contact layer 202 during negative-pressure therapy, for example, about 3 mm. By controlling the height of the nodules 902, the forces applied to the debris 704 by the contact layer 202 can be adjusted and the degree that the debris 704 is stretched can be varied.

In some embodiments, the formation of the nodules 902 can cause the debris 704 to remain in contact with a tissue interface 114 during negative pressure therapy. For example, the nodules 902 may contact the sidewalls of the through-holes 210 of the contact layer 202, while the surrounding tissue may contact the film layer 204 coating the second surface 208 of the contact layer 202. Similarly, the film layer 204 may be in contact with the debris 704 throughout therapy. The film layer 204 can provide a continuous application of antimicrobial/antibacterial agents to the debris 704, allowing the antimicrobial/antibacterial properties of the film layer 204 to remain effective throughout therapy. In some embodiments, formation of the nodules 902 may lift debris 704 and particulates off of the surrounding tissue, operating in a piston-like manner to move debris 704 toward the retainer layer 1002 and out of the sealed environment.

In response to the return of the sealed environment to ambient pressure by venting the sealed environment, the debris 704 and the subcutaneous tissue 706 may leave the through-holes 210, returning to the position shown in FIG. 7

In some embodiments, repeated application of negative-pressure therapy and instillation therapy while the contact layer 202 is disposed over the debris 704 may disrupt the debris 704, allowing the debris 704 to be removed during dressing changes. In other embodiments, the contact layer 202 may disrupt the debris 704 so that the debris 704 can be removed by negative pressure. In still other embodiments, the contact layer 202 may disrupt the debris 704, aiding removal of the debris 704 during debridement processes. With each cycle of therapy, the contact layer 202 may form nodules 902 in the debris 704. The formation of the nodules 902 and release of the nodules 902 by the contact layer 202 during therapy may disrupt the debris. With each subsequent cycle of therapy, disruption of the debris 704 can be increased.

Disruption of the debris 704 can be caused, at least in part, by the concentrated forces applied to the debris 704 by the through-holes 210 and the walls 302 of the contact layer 202. The forces applied to the debris 704 can be a function of the negative pressure supplied to the sealed environment and the area of each through-hole 210. For example, if the negative pressure supplied to the sealed environment is about 125 mmHg and the diameter of each through-hole 210 is about 5 mm, the force applied at each through-hole 210 is about 0.07 lbs. If the diameter of each through-hole 210 is increased to about 8 mm, the force applied at each through-hole 210 can increase up to 6 times. Generally, the relationship between the diameter of each through-hole 210 and the applied force at each through-hole 210 is not linear and can increase exponentially with an increase in diameter.

In some embodiments, the negative pressure applied by the negative-pressure source 102 may be cycled rapidly. For example, negative pressure may be supplied for a few seconds, then vented for a few seconds, causing a pulsation of negative pressure in the sealed environment. The pulsation of the negative pressure can pulsate the nodules 902, causing further disruption of the debris 704.

In some embodiments, the cyclical application of instillation therapy and negative pressure therapy may cause micro-floating. For example, negative pressure may be applied to the sealed environment during a negative-pressure therapy cycle. Following the conclusion of the negative-pressure therapy cycle, instillation fluid may be supplied during the instillation therapy cycle. The instillation fluid may cause the contact layer 202 to float relative to the debris. As the contact layer 202 floats, it may change position relative to the position the contact layer 202 occupied during the negative-pressure therapy cycle. The position change may cause the contact layer 202 to engage a slightly different portion of the debris 704 during the next negative-pressure therapy cycle, aiding disruption of the debris 704 and the application of antimicrobial/antibacterial agents by the film layer 204.

In some embodiments, the contact layer 202 may be provided as a component of a dressing kit. The kit may include a punch, and the contact layer 202 may be provided without any through-holes 210. When using the contact layer 202, the user may use the punch to place the through-holes 210 through portions of the contact layer 202 that may be placed over the debris. The kit provides a user, such as a clinician, the ability to customize the contact layer 202 to the particular tissue site, so that the through-holes 210 are only disrupting the debris and not healthy tissue that may be near or surround the debris.

The through-holes 210 of the contact layer 202 may generate concentrated stresses that influence disruption of the debris in different ways. For example, different shapes of the through-holes 210 may also focus the stresses generated by the contact layer 202 in advantageous areas. A lateral force, such as the lateral force 404, generated by a contact layer, such as the contact layer 202, may be related to a compressive force generated by applying negative pressure at a therapy pressure to a sealed therapeutic environment. For example, the lateral force 404 may be proportional to a product of a therapy pressure (TP) in the sealed environment, the compressibility factor (CF) of the contact layer 202, and a surface area (A) the second surface 208 of the contact layer 202. The relationship is expressed as follows:

$$\text{Lateral force } \alpha(TP*CF*A)$$

In some embodiments, the therapy pressure TP is measured in $N/m^2$, the compressibility factor (CF) is dimensionless, the area (A) is measured in $m^2$, and the lateral force is measured in Newtons (N). The compressibility factor (CF) resulting from the application of negative pressure to a contact layer may be, for example, a dimensionless number that is proportional to the product of the void space percentage (VS) of a contact layer, the firmness factor (FF) of the contact layer, the strut angle (SA) of the through-holes in the contact layer, and the perforation shape factor (PSF) of the through-holes in the contact layer. The relationship is expressed as follows:

$$\text{Compressibility Factor } (CF)\alpha(VS*FF*\sin(SA)*PSF)$$

Based on the above formulas, contact layers formed from different materials with through-holes of different shapes were manufactured and tested to determine the lateral force of the contact layers. For each contact layer, the therapy pressure TP was about −125 mmHg and the dimensions of the contact layer were about 200 mm by about 53 mm so that the surface area (A) of the tissue-facing surface of the contact layer was about 106 $cm^2$ or 0.0106 $m^2$. Based on the two equations described above, the lateral force for a Supracor® contact layer 202 having a firmness factor (FF) of 3 was about 13.3 where the Supracor® contact layer 202 had hexagonal through-holes 210 with a distance between opposite vertices of 5 mm, a perforation shape factor (PSF) of 1.07, a strut angle (SA) of approximately 66°, and a void space percentage (VS) of about 55%. A similarly dimensioned V.A.C.® GRANUFOAM™ Dressing contact layer 202 generated the lateral force 404 of about 9.1 Newtons (N).

TABLE 1

| Material | VS | FF | SA | Hole Shape | PSF | Major diam. (mm) | Lateral force |
|---|---|---|---|---|---|---|---|
| V.A.C. ® GRANUFOAM ™ Dressing | 56 | 5 | 47 | Ovular | 1 | 10 | 13.5 |
| Supracor ® | 55 | 3 | 66 | Hexagon | 1.1 | 5 | 13.3 |
| V.A.C. ® GRANUFOAM ™ Dressing | 40 | 5 | 63 | Triangle | 1.1 | 10 | 12.2 |
| V.A.C. ® GRANUFOAM ™ Dressing | 54 | 5 | 37 | Circular | 1 | 5 | 11.9 |
| V.A.C. ® GRANUFOAM ™ Dressing | 52 | 5 | 37 | Circular | 1 | 20 | 10.3 |
| Grey Foam | N/A | 5 | N/A | Horizontal stripes | N/A | N/A | 9.2 |
| V.A.C. ® GRANUFOAM ™ Dressing | 55 | 5 | 66 | Hexagon | 1.1 | 5 | 9.1 |
| V.A.C. ® GRANUFOAM ™ Dressing | N/A | 5 | N/A | Horizontal stripes | N/A | N/A | 8.8 |
| Zotefoam | 52 | 3 | 37 | Circular | 1 | 10 | 8.4 |
| V.A.C. ® GRANUFOAM ™ Dressing | 52 | 5 | 37 | Circular | 1 | 10 | 8.0 |
| V.A.C ® GRANUFOAM ™ Dressing | 52 | 5 | 64 | Circular | 1 | 10 | 7.7 |
| V.A.C. ® GRANUFOAM ™ Dressing | 56 | 5 | 66 | Hexagon | 1.1 | 10 | 7.5 |

TABLE 1-continued

| Material | VS | FF | SA | Hole Shape | PSF | Major diam. (mm) | Lateral force |
|---|---|---|---|---|---|---|---|
| Grey Foam | N/A | 3 | N/A | Horizontal stripes | N/A | N/A | 7.2 |
| Zotefoam | 52 | 3 | 52 | Circular | 1 | 20 | 6.8 |
| V.A.C. ® GRANUFOAM ™ Dressing | N/A | 3 | N/A | Horizontal Striping | N/A | N/A | 6.6 |
| V.A.C. ® GRANUFOAM ™ Dressing | 52 | 5 | 52 | Circular | 1 | 20 | 6.5 |
| V.A.C. ® GRANUFOAM ™ Dressing | N/A | 5 | N/A | Vertical Stripes | N/A | N/A | 6.1 |
| V.A.C. ® GRANUFOAM ™ Dressing | N/A | 1 | N/A | None | N/A | N/A | 5.9 |
| V.A.C. ® GRANUFOAM ™ Dressing | N/A | 3 | N/A | Vertical stripes | N/A | N/A | 5.6 |
| V.A.C. ® GRANUFOAM ™ Dressing | 52 | 1 | 37 | None | 1 | 10 | 5.5 |

In some embodiments, the formulas described above may not precisely describe the lateral forces due to losses in force due to the transfer of the force from the contact layer to the wound. For example, the modulus and stretching of the cover 116, the modulus of the tissue site, slippage of the cover 116 over the tissue site, and friction between the contact layer 202 and the tissue site may cause the actual value of the lateral force 404 to be less than the calculated value of the lateral force 404.

Figure 10:
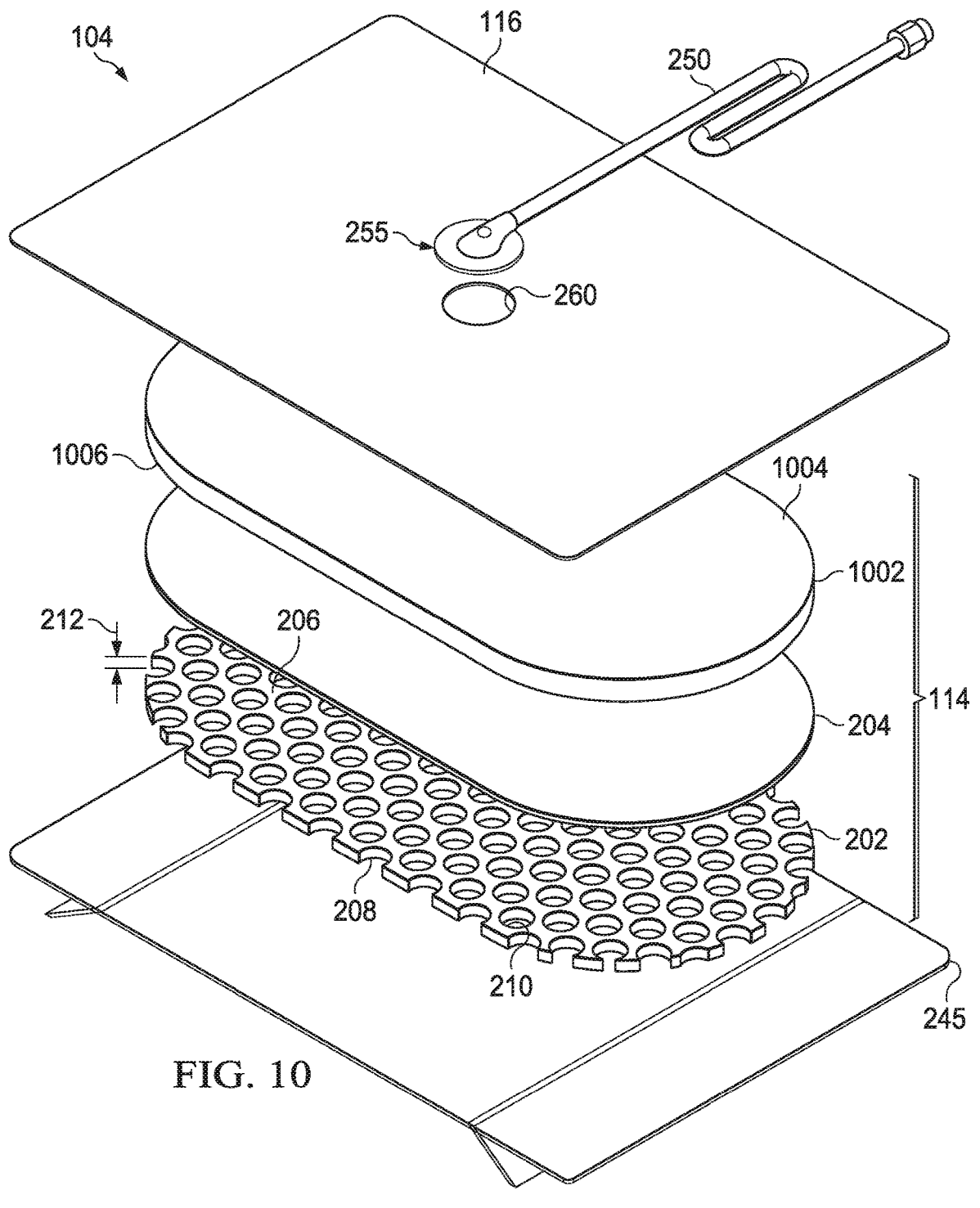
FIG. 10 is an assembly view of an example of a dressing of FIG. 1, illustrating additional details that may be associated with some embodiments in which a tissue interface comprises multiple layers.

FIG. 10 is an assembly view of an example of the dressing 104 of FIG. 1, illustrating additional details that may be associated with some embodiments in which the tissue interface 114 comprises multiple layers. In some embodiments, the tissue interface 114 can include the contact layer 202, the film layer 204, and a retainer layer 1002. The contact layer 202 may have the first surface 206, the second surface 208, the plurality of through-holes 210 extending through the contact layer 202 from the first surface 206 to the second surface 208, and the thickness 212. The retainer layer 1002 can have a first surface 1004 and a second surface 1006 on an opposite side of the retainer layer 1002 from the first surface 1004. The film layer 204 may be disposed adjacent to the second surface 1006 of the retainer layer 1002. In some embodiments, the film layer 204 can be coupled to the second surface 1006 of the retainer layer 1002. In some embodiments, the retainer layer 1002 may be positioned over the contact layer 202. In other embodiments, the retainer layer 1002 may be positioned over the contact layer 202, and if the depth of the tissue site is greater than a thickness of the retainer layer 1002 and the thickness 212 of the contact layer 202 combined, another retainer layer 1002 may be placed over the contact layer 202 and the retainer layer 1002.

In some embodiments, the retainer layer 1002 may be a foam having pore sizes in a range of about 60 microns to about 2000 microns. In other embodiments, the retainer layer 1002 may be a foam having pore sizes in a range of about 400 microns to about 600 microns. The tensile strength of the retainer layer 1002 may also vary according to needs of a prescribed therapy. For example, the tensile strength of a foam may be increased for instillation of topical treatment solutions. In one non-limiting example, the retainer layer 1002 may be an open-cell, reticulated polyurethane foam such as V.A.C.® GRANUFOAM™ Dressing available from Kinetic Concepts, Inc. of San Antonio, Texas; in other embodiments the retainer layer 1002 may be an open-cell, reticulated polyurethane foam such as a V.A.C. VERAFLO™ dressing, also available from Kinetic Concepts, Inc., of San Antonio, Texas. In other embodiments, the retainer layer 1002 may be formed of an un-reticulated open-cell foam.

In some embodiments, the retainer layer 1002 may be an open-cell reticulated foam having a thin layer of silver coated onto the foam to form the film layer 204. In other embodiments, the film layer 204 can be formed from citric acid or acetic acid. For example, the film layer 204 can be a 100 millimolar ("mM") citric acid or a 100 millimolar ("mM") acetic acid. The film layer 204 can be coated onto the second surface 1006 of the retainer layer 1002. For example, the second surface 1006 of the retainer layer 1002 can be placed into a tray having the solution of the citric acid or the acetic acid while the solution cures into the film layer 204. In other embodiments, the solution of the citric acid or the acetic acid can be produced in sheets. The sheets can be positioned over the second surface 1006 of the retainer layer 1002 and placed in contact with the second surface 1006. The natural tackiness of the citric acid and the acetic acid can couple the sheet to the retainer layer 1002 and form the film layer 204. For example, the tackiness of the citric acid or the acetic acid sheet of the film layer 204 can bond the film layer 204 to the retainer layer 1002.

As illustrated in the example of FIG. 10, in some embodiments, the dressing 104 may include a release liner 245 to protect an optional adhesive on a portion of the cover 116 prior to use. The release liner 245 may also provide stiffness to assist with, for example, deployment of the dressing 104. FIG. 10 also illustrates one example of a fluid conductor 250 and a dressing interface 255. As shown in the example of FIG. 2, the fluid conductor 250 may be a flexible tube, which can be fluidly coupled on one end to the dressing interface 255. The dressing interface 255 may be an elbow connector, as shown in the example of FIG. 2, which can be placed over an aperture 260 in the cover 116 to provide a fluid path between the fluid conductor 250 and the tissue interface 114.

Figure 11:
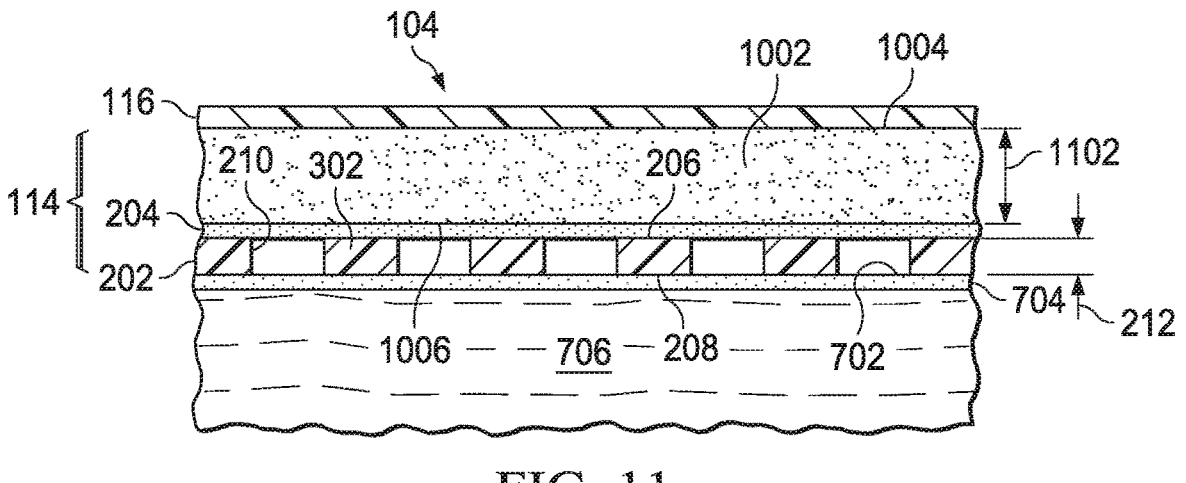
FIG. 11 is a sectional view of a portion of the contact layer of FIG. 10, illustrating additional details that may be associated with some embodiments.

FIG. 11 is a sectional view of a portion of the contact layer 202, illustrating additional details that may be associated with some embodiments. The contact layer 202, the film layer 204, and the retainer layer 1002 may be placed at the tissue site 702 having the debris 704 covering the subcutaneous tissue 706. The film layer 204 can be coupled to the second surface 1006 of the retainer layer 1002. The cover 116 may be placed over the retainer layer 1002 to provide the sealed environment for the application of negative-pressure therapy or instillation therapy. As shown in FIG. 11, the retainer layer 1002 may have a thickness 1102 if the pressure in the sealed environment is about an ambient pressure. In some embodiments, the thickness 1102 may be about 8 mm. In other embodiments, the thickness 1102 may be about 16 mm.

Figure 12:
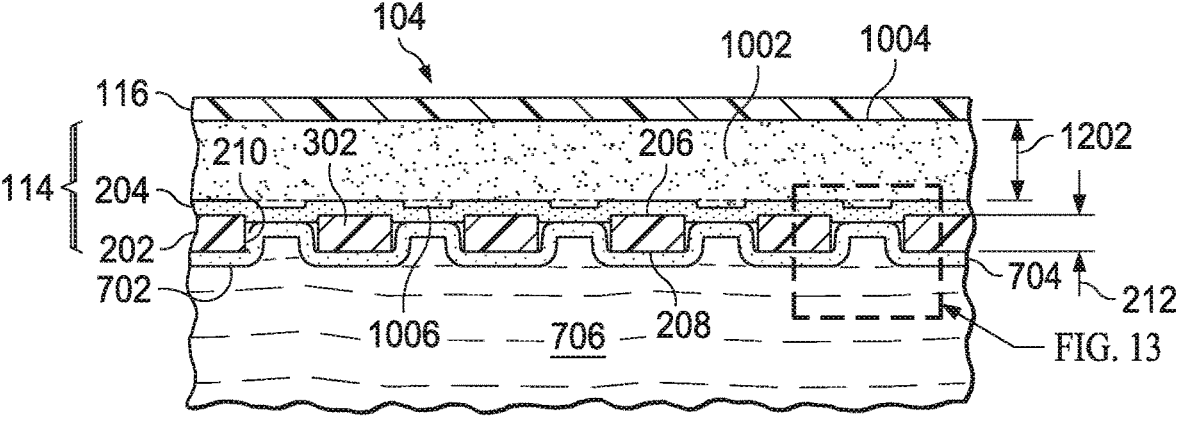
FIG. 12 is a sectional view of a portion of the contact layer of FIG. 10 during negative-pressure therapy, illustrating additional details that may be associated with some embodiments.

FIG. 12 is a sectional view of a portion of the dressing 104 during negative-pressure therapy, illustrating additional details that may be associated with some embodiments. For example, FIG. 12 may illustrate a moment in time where a pressure in the sealed environment may be about 125 mmHg of negative pressure. In some embodiments, the retainer layer 1002 may be a non-felted foam, and the contact layer 202 may be a felted foam. In response to the application of negative pressure, the contact layer 202 may not compress, and the retainer layer 1002 may compress so that the manifold has a thickness 1202. In some embodiments, the thickness 1202 of the retainer layer 1002 during negative-pressure therapy may be less than the thickness 1102 of the retainer layer 1002 if the pressure in the sealed environment is about the ambient pressure.

In some embodiments, negative pressure in the sealed environment can generate concentrated stresses in the retainer layer 1002 and the film layer 204 adjacent to the through-holes 210 in the contact layer 202. The concentrated stresses can cause macro-deformation of the retainer layer 1002 and the film layer 204 that draws portions of the retainer layer 1002 and the film layer 204 into the through-holes 210 of the contact layer 202. Similarly, negative pressure in the sealed environment can generate concentrated stresses in the debris 704 adjacent to the through-holes 210 in the contact layer 202. The concentrated stresses can cause macro-deformations of the debris 704 and the subcutaneous tissue 706 that draws portions of the debris 704 and the subcutaneous tissue 706 into the through-holes 210.

Figure 13:
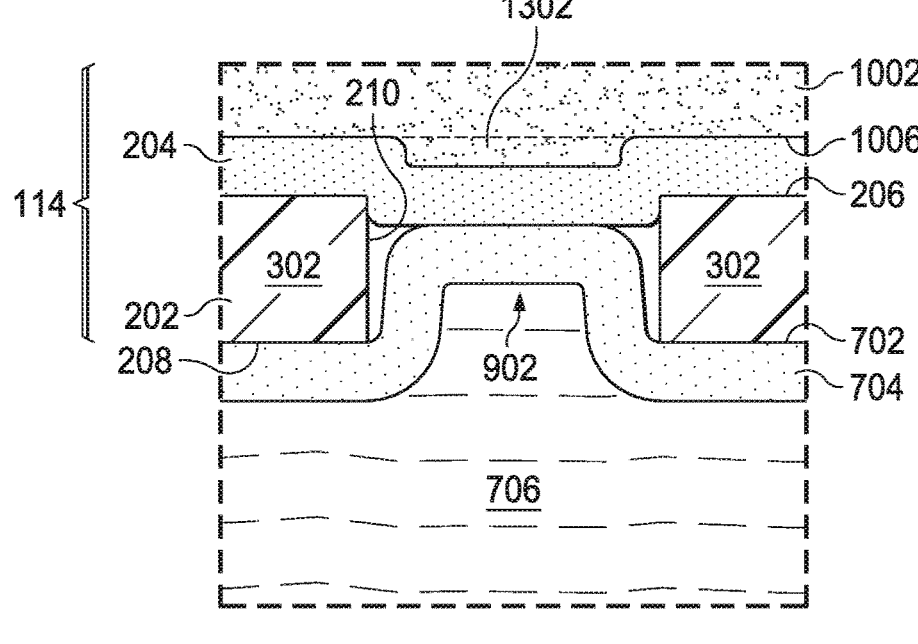
FIG. 13 is a detail view of the contact layer of FIG. 10, illustrating additional details of the operation of the contact layer during negative-pressure therapy.

FIG. 13 is a detail view of the contact layer 202, illustrating additional details of the operation of the contact layer 202 during negative-pressure therapy. Portions of the retainer layer 1002 and the film layer 204 in contact with the first surface 206 of the contact layer 202 may be drawn into the through-holes 210 to form bosses 1302. The bosses 1302 may have a shape that corresponds to the through-holes 210. A height of the bosses 1302 from the retainer layer 1002 may be dependent on the pressure of the negative pressure in the sealed environment, the area of the through-holes 210, and the firmness factor of the retainer layer 1002. Similarly, the through-holes 210 of the contact layer 202 may create macro-pressure points in portions of the debris 704 and the subcutaneous tissue 706 that are in contact with the second surface 208 of the contact layer 202, causing tissue puckering and formation of the nodules 902 in the debris 704 and the subcutaneous tissue 706.

In some embodiments, the retainer layer 1002 may limit the height of the nodules 902 to the thickness 212 of the contact layer 202 under negative pressure if the contact layer 202 is compressible. In other embodiments, the bosses 1302 of the retainer layer 1002 may limit the height of the nodules 902 to a height that is less than the thickness 212 of the contact layer 202. By controlling the firmness factor of the retainer layer 1002, the height of the bosses 1302 over the surrounding material of the retainer layer 1002 can be controlled. The height of the nodules 902 can be limited to the difference of the thickness 212 of the contact layer 202 and the height of the bosses 1302. In some embodiments, the height of the bosses 1302 can vary from zero to several millimeters as the firmness factor of the retainer layer 1002 decreases. In an exemplary embodiment, the thickness 212 of the contact layer 202 may be about 7 mm. During the application of negative pressure, the bosses 1302 may have a height between about 4 mm to about 5 mm, limiting the height of the nodules to about 2 mm to about 3 mm. By controlling the height of the nodules 902 by controlling the thickness 212 of the contact layer 202, the firmness factor of the retainer layer 1002, or both, the aggressiveness of disruption to the debris 704 and tearing can be controlled.

The bosses 1302 and the nodules 902 place the debris 704 into contact with the film layer 204. In some embodiments, the nodules 902 and the bosses 1302 trap the bacterial material that may reside in the debris 704 against the film layer 204 drawn into the through-holes 210 by the bosses 1302. For example, portions of the film layer 204 can be drawn into the through-holes 210 by the bosses 1302, positioning the film layer 204 in contact with debris 704. The film layer 204 may be spaced from both the tissue site 702 and the cover 116, extending the usable life of the film layer 204. The antimicrobial/antibacterial properties of the film layer 204 can apply antimicrobial/antibacterial agents to the debris 704 that limit and inhibit the growth of bacteria, microbes, and other entities that can slow or inhibit healing. Furthermore, as the debris 704 and the tissue are torn or cracked by the application of negative-pressure therapy, the antimicrobial/antibacterial properties of the film layer 204 can prevent the development of infection in the newly opened areas of tissue.

In response to the return of the sealed environment to ambient pressure by venting the sealed environment, the nodules 902 and the bosses 1302 may leave the through-holes 210, returning to the position shown in FIG. 11.

Figure 14:
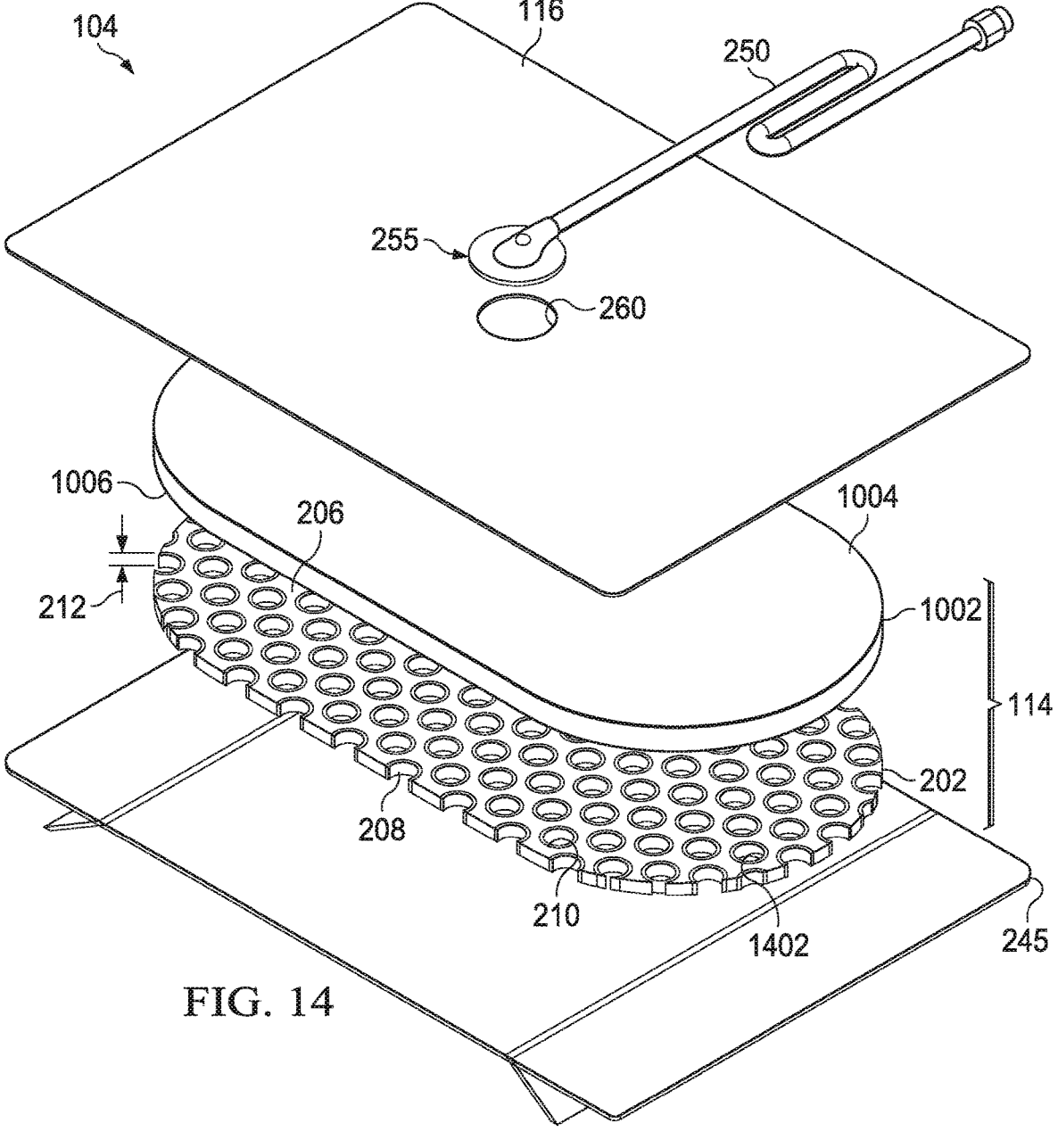
FIG. 14 is an assembly view of an example of a dressing of FIG. 1, illustrating additional details that may be associated with some embodiments in which a tissue interface comprises multiple layers.

FIG. 14 is an assembly view of an example of the dressing 104 of FIG. 1, illustrating additional details that may be associated with some embodiments in which the tissue interface 114 comprises multiple layers. In some embodiments, the tissue interface 114 can include the contact layer 202 and a cover layer or a retainer layer 1002. The contact layer 202 may have the first surface 206, the second surface 208, the plurality of through-holes 210 extending through the contact layer 202 from the first surface 206 to the second surface 208, and the thickness 212. The retainer layer 1002 can have the first surface 1004 and the second surface 1006. In some embodiments, the retainer layer 1002 may be positioned over the contact layer 202. In other embodiments, the retainer layer 1002 may be positioned over the contact layer 202, and if the depth of the tissue site is greater than a thickness of the retainer layer 1002 and the thickness 212 of the contact layer 202 combined, another retainer layer 1002 may be placed over the contact layer 202 and the retainer layer 1002.

In some embodiments, the film layer 204 can comprise a coating 1402 disposed on the interior surfaces of the walls 302. The interior surfaces of the walls 302 can also be referred to as the sidewalls of the through-holes 210. The coating 1402 can comprise a thin layer of silver coated onto the through-holes 210. In other embodiments, the coating 1402 can be formed from citric acid or acetic acid. For example, the coating 1402 can be a 100 millimolar ("mM") citric acid or a 100 millimolar ("mM") acetic acid.

As illustrated in the example of FIG. 14, in some embodiments, the dressing 104 may include the release liner 245, the fluid conductor 250, and the dressing interface 255, which can be placed over the aperture 260 in the cover 116 to provide a fluid path between the fluid conductor 250 and the tissue interface 114.

Figure 15:
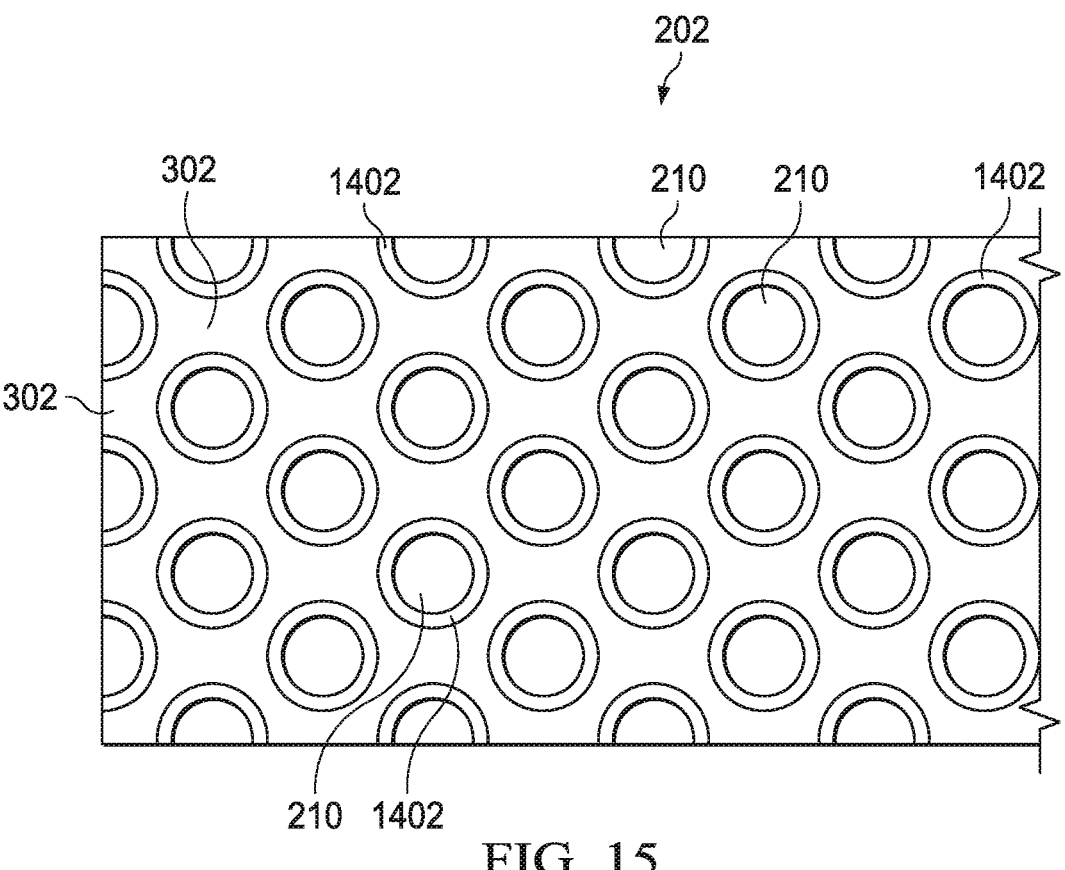
FIG. 15 is a plan view illustrating additional details of a portion of the contact layer of FIG. 14.

FIG. 15 is a plan view illustrating additional details of a portion of the contact layer 202 of FIG. 14. In FIG. 15, a portion of the contact layer 202 of FIG. 14 is shown. The contact layer 202 may include the plurality of through-holes 210 aligned in parallel rows to form an array. The coating 1402 can be coupled to the interior surfaces of the walls 302. In some embodiments, the coating 1402 can substantially coat the interior surfaces of the walls 302 between the first surface 206 and the second surface 208. The coating 1402 can be a thin layer of silver coated onto the interior surfaces of the walls 302. The silver coating of the coating 1402 may have a thickness of about 1 micron to about 10 microns and, in particular, about 3 microns. The silver of the coating 1402 may be 99.9% pure metallic silver that is bonded to the interior surfaces of the walls 302.

In some embodiments, the coating 1402 can be a citric acid or an acetic acid. The contact layer 202 can be submerged into a tray having the solution of the citric acid or the acetic acid previously described. The solution can cure into the coating 1402 covering the submerged surfaces of the contact layer 202. The first surface 206 and the second surface 208 can be shaved or otherwise planed to remove the coating 1402 from the first surface 206 and the second surface 208. If necessary, the through holes 210 can be re-cut or drilled to form the coating 1402 having a thickness between 100 microns and about 500 microns. In other embodiments, the thickness of the coating can be reduced, for example, the coating 1402 could have a thickness between about 1 micron and about 10 microns and preferably about 3 microns. In other embodiments, the solution of the citric acid or the acetic acid can be produced in sheets. The sheets can be positioned over the contact layer 202 and placed in contact with the interior surfaces of the walls 302. Material not in contact with the interior surfaces of the walls 302 can be removed to leave the first surface 206 and the second surface 208 free from the coating 1402. The natural tackiness of the sheet formed from the citric acid and the acetic acid can couple the sheet to the interior surfaces of the walls 302 of the contact layer 202. In some embodiments, the average effective diameter of the through-holes 210 is between about 5 mm and about 20 mm and, more specifically, about 10 mm following the addition of the coating 1402.

Figure 16:
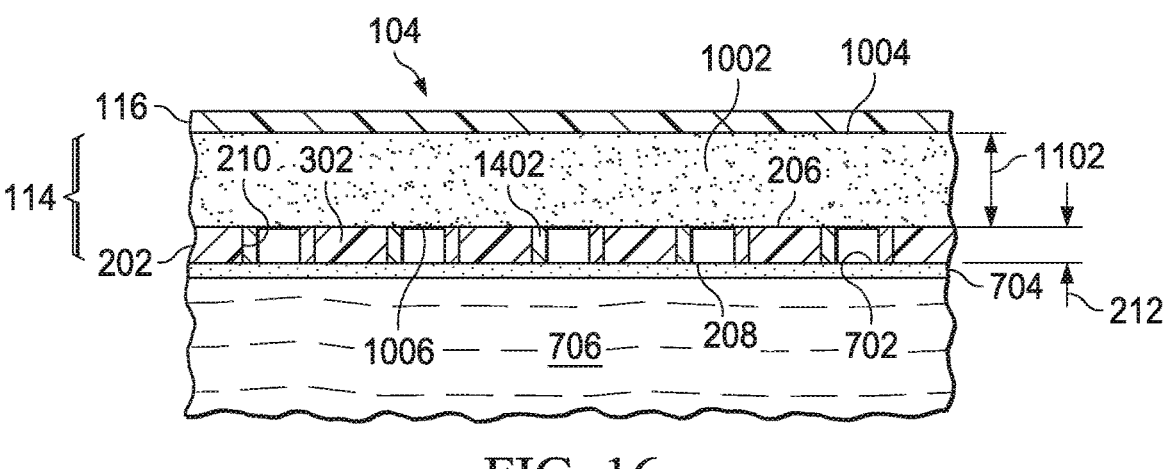
FIG. 16 is a sectional view of a portion of the contact layer of FIG. 14, illustrating additional details that may be associated with some embodiments.

FIG. 16 is a sectional view of a portion of the contact layer 202, illustrating additional details that may be associated with some embodiments. The contact layer 202 having the coating 1402 and the retainer layer 1002 may be placed at the tissue site 702 having the debris 704 covering the subcutaneous tissue 706. The cover 116 may be placed over the retainer layer 1002 to provide the sealed environment for the application of negative-pressure therapy or instillation therapy. As shown in FIG. 16, the retainer layer 1002 may have the thickness 1102 if the pressure in the sealed environment is about an ambient pressure.

Figure 17:
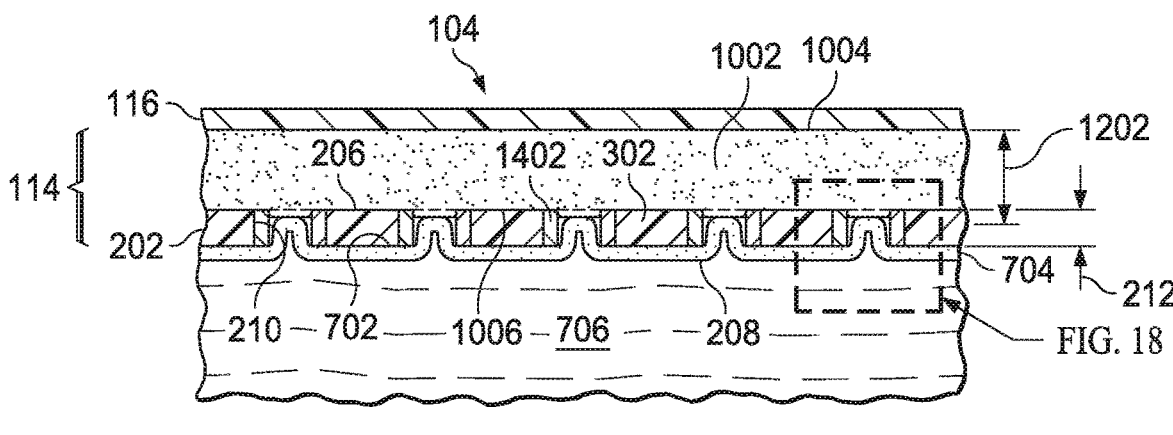
FIG. 17 is a sectional view of a portion of the contact layer of FIG. 14 during negative-pressure therapy, illustrating additional details that may be associated with some embodiments.

FIG. 17 is a sectional view of a portion of the dressing 104 during negative-pressure therapy, illustrating additional details that may be associated with some embodiments. For example, FIG. 17 may illustrate a moment in time where a pressure in the sealed environment may be about 125 mmHg of negative pressure. In some embodiments, the retainer layer 1002 may be a non-felted foam, and the contact layer

202 may be a felted foam. In response to the application of negative pressure, the contact layer 202 may not compress, and the retainer layer 1002 may compress so that the manifold has a thickness 1202. In some embodiments, the thickness 1202 of the retainer layer 1002 during negative-pressure therapy may be less than the thickness 1102 of the retainer layer 1002 if the pressure in the sealed environment is about the ambient pressure.

In some embodiments, negative pressure in the sealed environment can generate concentrated stresses in the retainer layer 1002 and the film layer 204 adjacent to the through-holes 210 in the contact layer 202. The concentrated stresses can cause macro-deformation of the retainer layer 1002 that draws portions of the retainer layer 1002 into the through-holes 210 of the contact layer 202. Similarly, negative pressure in the sealed environment can generate concentrated stresses in the debris 704 adjacent to the through-holes 210 in the contact layer 202. The concentrated stresses can cause macro-deformations of the debris 704 and the subcutaneous tissue 706 that draws portions of the debris 704 and the subcutaneous tissue 706 into the through-holes 210.

Figure 18:
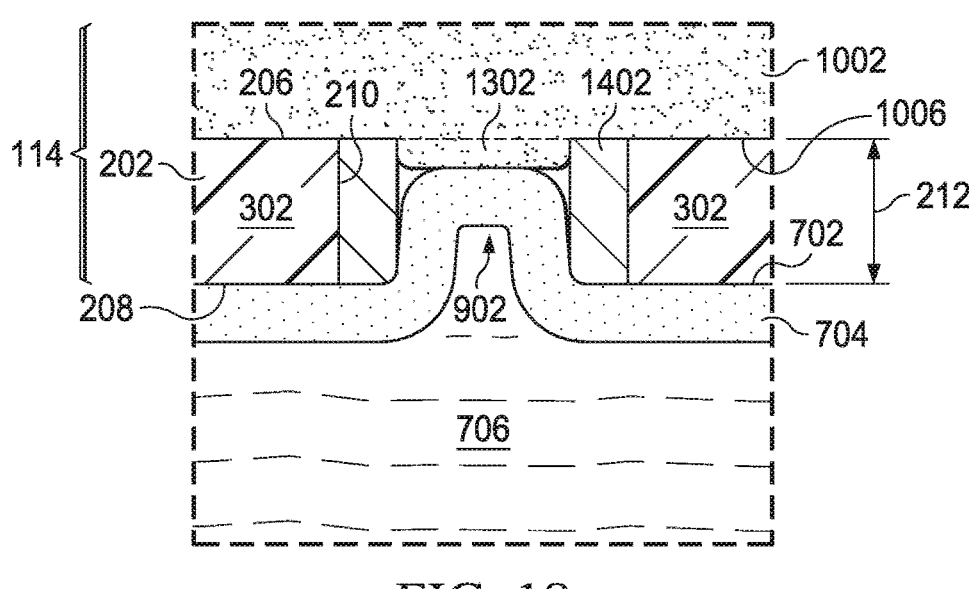
FIG. 18 is a detail view of the contact layer of FIG. 14, illustrating additional details of the operation of the contact layer during negative-pressure therapy.

FIG. 18 is a detail view of the contact layer 202, illustrating additional details of the operation of the contact layer 202 during negative-pressure therapy. Portions of the retainer layer 1002 in contact with the first surface 206 of the contact layer 202 may be drawn into the through-holes 210 to form the bosses 1302. Similarly, the through-holes 210 of the contact layer 202 may create macro-pressure points in portions of the debris 704 and the subcutaneous tissue 706 that are in contact with the second surface 208 of the contact layer 202, causing tissue puckering and the formation of the nodules 902 in the debris 704 and the subcutaneous tissue 706. The bosses 1302 and the nodules 902 place the debris 704 into contact with the coating 1402 on the interior surfaces of the walls 302. In some embodiments, formation of the nodules 902 and the bosses 1302 may press the bacterial material that may reside in the debris 704 against the coating 1402. As the debris 704 and the associated bacterial material is forced into contact with the coating 1402 and the debridement process occurs, the coating 1402 can have increased exposure to portions of the debris 704 that may be cracked or torn by the debridement process. The antimicrobial/antibacterial properties of the coating 1402 can apply antimicrobial/antibacterial agents to the debris 704 that limit and inhibit the growth of bacteria, microbes, and other entities that can slow or inhibit healing to the cracked and torn portions of the debris 704. The antimicrobial/antibacterial properties of the film layer 204 can prevent the re-development of infection in the newly exposed areas of tissue. In response to the return of the sealed environment to ambient pressure by venting the sealed environment, the debris 704 and the subcutaneous tissue 706 may leave the through-holes 210, returning to the position shown in FIG. 16.

In some embodiments, the tissue interface 114 can include both the film layer 204 and the coating 1402. For example, the film layer 204 can be coated to the second surface 208 of the contact layer 202 or the second surface 1006 of the retainer layer 1002, and the coating 1402 can be coupled to the interior surface of the walls 302 of the contact layer 202. In some embodiments, the tissue interface 114 can include a first film layer 204 coated to the second surface 208 of the contact layer 202, a second film layer 204 coated to the second surface 1006 of the retainer layer 1002, and the coating 1402 can be coupled to the interior surface of the walls 302 of the contact layer 202. In still other embodiments, additional retainer layers 1002 having additional film layers 204 can be added to the tissue interface 114 as needed to substantially fill the tissue site. In embodiments having one or more film layers 204 and the coating 1402, the film layers 204 and the coating 1402 can be formed from the same material, for example, silver, citric acid, or acetic acid. The one or more film layers 204 and the coating 1402 can also be formed from different materials for example, the first film layer 204 can be formed from silver, the coating 1402 can be formed from citric acid, and if included, the second of other additional film layers 204 can be formed from acetic acid or any combination thereof.

The systems, apparatuses, and methods described herein may provide significant advantages. For example, combining the mechanical rubbing action of a contact layer with the hydrating and flushing action of instillation and negative-pressure therapy may enable low or no pain debridement of a tissue site. A contact layer as described herein may also require less monitoring from a clinician or other attendant as compared to other mechanical debridement processes and enzymatic debridement processes. In addition, contact layers as described herein may not become blocked by removed necrotic tissue as may occur during autolytic debridement of a tissue site. Furthermore, the contact layers described herein can aid in removal of necrosis, eschar, impaired tissue, sources of infection, exudate, slough including hyperkeratosis, pus, foreign bodies, debris, and other types of bioburden or barriers to healing. The contact layers can also decrease odor, excess wound moisture, and the risk of infection while stimulating edges of a tissue site and epithelialization. The contact layers described herein can also provide improved removal of thick exudate, allow for earlier placement of instillation and negative-pressure therapy devices, may limit or prevent the use of other debridement processes, and can be used on tissue sites that are difficult to debride.

The film layer and the coating described herein can provide continuous delivery of antibacterial/antimicrobial agents direct to the area in contact with the tissue site. The dressings are easy to use, provide effective protection to reduce bacteria (aerobic, anaerobic, gram positive and negative), yeast, and fungi and can reduce infection. The dressing can also provide an effective barrier to bacterial penetration. The dressing can remove thick wound exudate and provide a wound cleansing option and decreasing bioburden.

In some embodiments, the therapy system may be used in conjunction with other tissue removal and debridement techniques. For example, the therapy system may be used prior to enzymatic debridement to soften the debris. In another example, mechanical debridement may be used to remove a portion of the debris at the tissue site, and the therapy system may then be used to remove the remaining debris while reducing the risk of trauma to the tissue site.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing, the container, or both may be eliminated or separated from other components for manufacture or sale. In other example configurations, the controller may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A dressing for treating a tissue site, the dressing comprising:

a debridement tool having a plurality of openings extending into the debridement tool to form interior surfaces perpendicular to and extending from a first surface of the debridement tool, the debridement tool configured to be positioned adjacent to the tissue site;

an antibacterial agent coupled to the interior surfaces of the plurality of openings of the debridement tool, the first surface being free from the antibacterial agent; and a drape configured to be positioned over the debridement tool to form a sealed space having the debridement tool disposed in the sealed space.

2. The dressing of claim 1, further comprising a retainer layer disposed over the debridement tool.

3. The dressing of claim 2, wherein the retainer layer has a first side and a second side, the second side configured to be positioned adjacent to the debridement tool, and the antibacterial agent comprises a first antibacterial agent, the dressing further comprising a second antibacterial agent coupled to the second side of the retainer layer.

4. The dressing of claim 3, wherein the first antibacterial agent is different than the second antibacterial agent.

5. The dressing of claim 1, wherein the debridement tool comprises a second surface opposite the first surface, the second surface configured to be positioned adjacent to the tissue site, and the antibacterial agent comprises a first antibacterial agent, the dressing further comprising a second antibacterial agent coupled to the second surface of the debridement tool.

6. The dressing of claim 5, wherein the first antibacterial agent is different than the second antibacterial agent.

* * * * *